(12) United States Patent
Greenbaum et al.

(10) Patent No.: US 8,209,024 B2
(45) Date of Patent: Jun. 26, 2012

(54) METHOD AND APPARATUS FOR TREATING ISCHEMIC DISEASES

(75) Inventors: Elias Greenbaum, Knoxville, TN (US); Mark S. Humayun, Glendale, CA (US)

(73) Assignees: UT-Battelle, LLC, Oak Ridge, TN (US); University of Southern California, Los Angeles, CA (US)

( * ) Notice: Subject to any disclaimer, the term of this patent is extended or adjusted under 35 U.S.C. 154(b) by 206 days.

(21) Appl. No.: 12/523,990

(22) PCT Filed: Jan. 22, 2008

(86) PCT No.: PCT/US2008/000742
§ 371 (c)(1),
(2), (4) Date: Mar. 16, 2010

(87) PCT Pub. No.: WO2008/091559
PCT Pub. Date: Jul. 31, 2008

(65) Prior Publication Data
US 2010/0168646 A1 Jul. 1, 2010

Related U.S. Application Data

(60) Provisional application No. 60/885,958, filed on Jan. 22, 2007.

(51) Int. Cl.
*A61N 1/00* (2006.01)
(52) U.S. Cl. .................. 607/53; 607/2; 607/50
(58) Field of Classification Search .......... 607/3, 53
See application file for complete search history.

(56) References Cited

U.S. PATENT DOCUMENTS

| | | | |
|---|---|---|---|
| 4,180,445 A | 12/1979 | Bennett et al. | |
| 5,213,570 A | 5/1993 | VanDeripe | |
| 6,901,296 B1 | 5/2005 | Whitehurst et al. | |
| 6,902,564 B2 | 6/2005 | Morgan et al. | |
| 7,813,807 B2 * | 10/2010 | Franklin | 607/53 |
| 2006/0217783 A1 | 9/2006 | Harold | |
| 2008/0116064 A1 | 5/2008 | Hashimoto et al. | |

OTHER PUBLICATIONS

Abdel Ghany et al. Oxygen evolution anodes composed of anodically deposited Mn-Mo-Fe oxides for seawater electrolysis. Electrochimica Acta 48 (2002) pp. 21-28.

Bennett, J.E. Electrodes for Generation of Hydrogen and Oxygen from Seawater. Int. J. Hydrogen Energy, vol. 5, pp. 401-408. Pergamon Press Ltd. 1980.

Song, et al. Preparation and Characterization of Manganese Dioxide Electrodes for Highly Selective Oxygen Evolution During Diluted Chloride Solution Electrolysis. J. Ind. Eng. Chem., vol. 13, No. 4, (2007) pp. 545-551.

(Continued)

*Primary Examiner* — Carl H Layno
*Assistant Examiner* — Paula J Stice
(74) *Attorney, Agent, or Firm* — McDermott Will & Emery LLP

(57) ABSTRACT

The present invention relates to the treatment of ischemic diseases, and more particularly, to treatment of diabetic retinopathy and ischemia of the retinal and choroidal tissues. The treatment, which will work in vitrectomized eyes as well as non-vitrectomized eyes, is based on selective and fractional electrolysis of the vitreous humor to produce oxygen and optionally active chlorine while simultaneously controlling pH. Oxygen or active chlorine can suppress or reverse the onset of diabetic retinopathy, other retinovascular diseases, and choroidal neovascularization.

11 Claims, 14 Drawing Sheets

OTHER PUBLICATIONS

Conway B.E. et al., "Kinetic and optical relaxation studies of adsorbed intermediate in some electrochemical reactions," *Faraday Discuss. Chem. Soc.* vol. 56, pp. 210-227 (1973). Abstract only.

Ahmed J. et al., "Oxygen distribution in the macaque retina," *Investigative Opthalmology & Visual Science*, vol. 34 (3), pp. 516-521 (Mar. 1993).

International Search Report and Written Opinion of the International Searching Authority, mailed May 19, 2008, for PCT Application No. PCT/US2008/000742.

Extended European Search Report, dated Dec. 28, 2011, for European Application No. 08713191.8-1269, entitled "Method and Apparatus for Treating Ischemic Diseases," based on PCT Application No. PCT/US2008/000742, published Jul. 31, 2008, as WO/2008/091559.

* cited by examiner

Retina
pH
O₂
14
16
10
12
Optic Nerve
Microconnector Cable
18

Combination pH, O₂ Probe
Electrolysis Power Supply Controlled by pH/O₂ Sensors
12
18
14
10
16

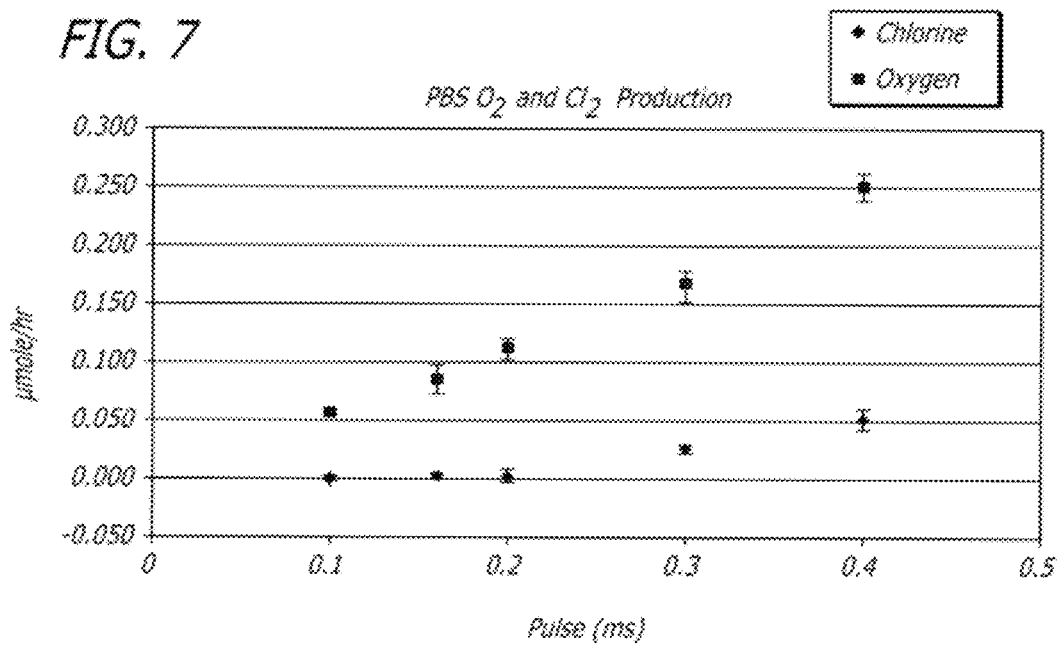
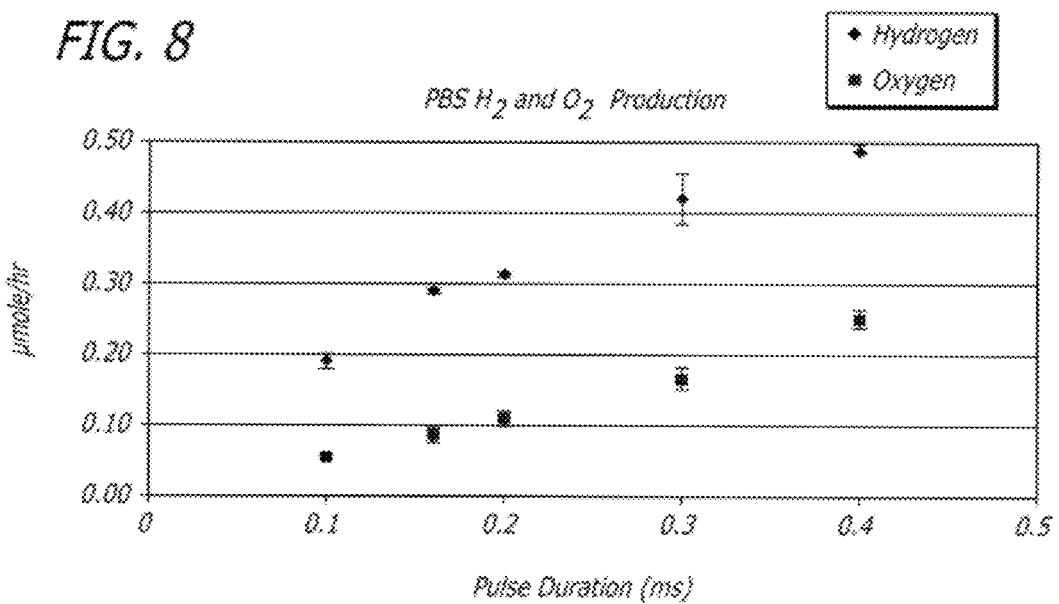

| RVO (N=4) | Baseline | Post Occlusion | p-Value |
|---|---|---|---|
| Oxygen Tension (mmHg) | | | |
| Pre-retinal | 20.4 (5.3) | 1.9 (3.3) | 0.006 |
| Mid-Vitreous | 11.1 (1.4) | 0.1 (0.3) | 0.0008 |
| OCT Edema (µM) | | | |
| Myelin Wing | 252 (37.2) | 326 (78.8) | 0.04 |
| VEGF Level (pg/ml) | | | |
| Vitreous | 32 (65) | 964 (536) | 0.02 |

| RVO (Oxygenation) | Pre-Oxygenation | Post-Oxygenation |
|---|---|---|
| Oxygen Tension (mmHg) | | |
| Pre-retinal | 5.2 | 39.0 (p=0.08) |
| Mid-Vitreous | 0.1 | 49.0 (p=0.04) |

FIG. 21
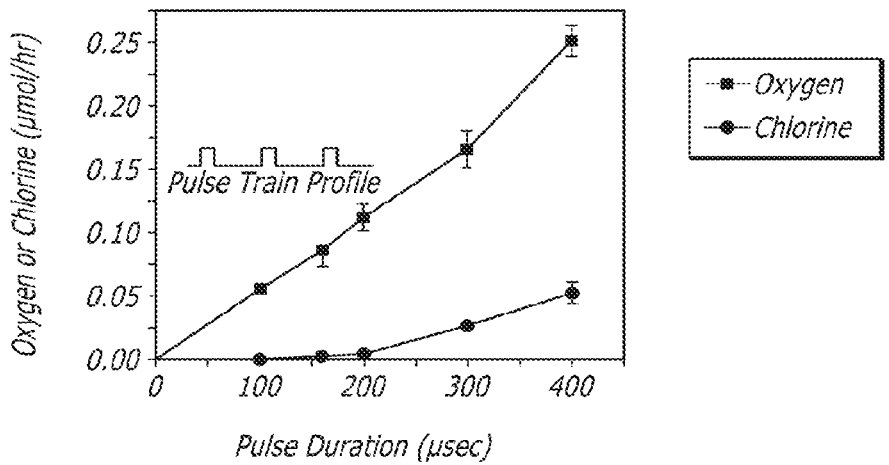
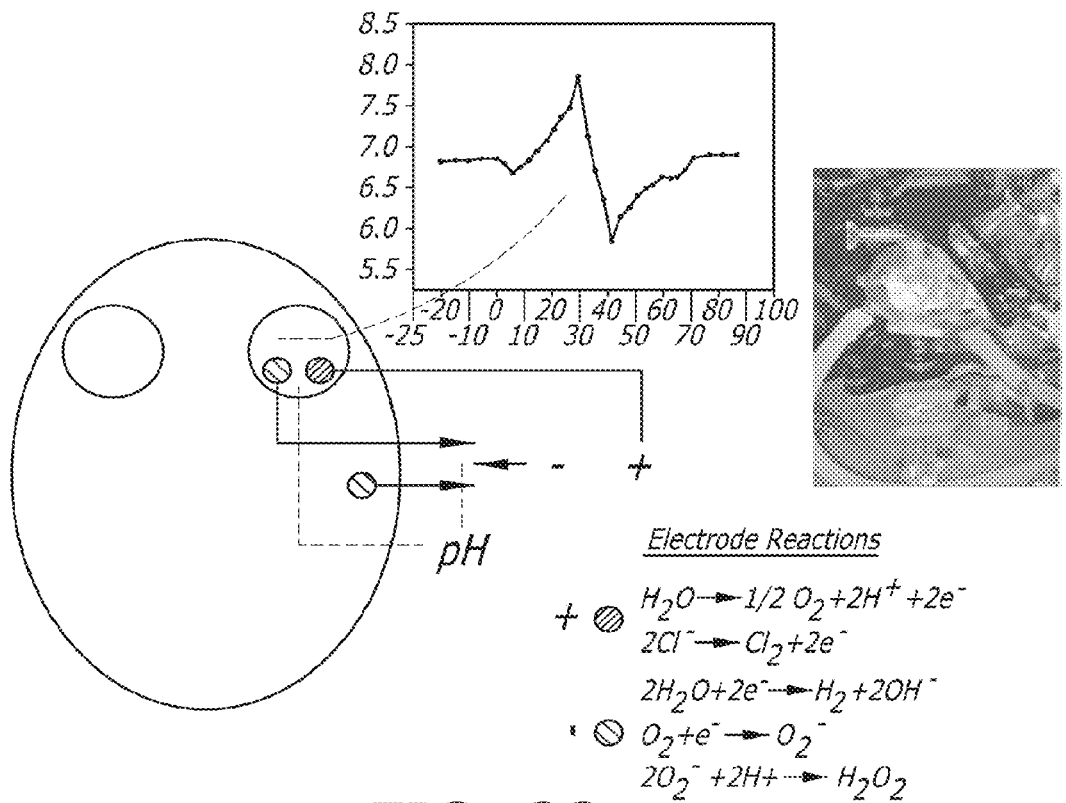
FIG. 22

METHOD AND APPARATUS FOR TREATING ISCHEMIC DISEASES

CROSS-REFERENCE TO RELATED APPLICATION

This application claims the benefit of U.S. Provisional Application Ser. No. 60/885,958, filed Jan. 22, 2007, and is a national filing of PCT Application No. PCT/US2008/000742, filed Jan. 22, 2008. The content of both of these applications is incorporated herein by reference in their entirety.

FIELD OF THE INVENTION

The present invention relates to methods and an apparatus for the treatment of ischemic diseases and more particularly to treatment of diabetic retinopathy and ischemia of other biological tissues.

BACKGROUND OF THE INVENTION

Diabetes is known to adversely affect the circulatory system of the retina. This usually occurs in several stages, two of which are background diabetic retinopathy and proliferative diabetic retinopathy. In the proliferative stage of diabetic retinopathy, poor circulation in the retina causes it to become oxygen-deprived (causing ischemia of the retinal and choroidal tissues). In response to this oxygen deprivation, neovascularization occurs, wherein vessels develop in an attempt to maintain sufficient oxygen in the retina. However, the newly-formed vessels are delicate and hemorrhage easily, leaking blood into the vitreous, thereby causing decreased vision. In latter stages of the disease, subsequent vessel growth and scar tissue can cause retinal detachment and glaucoma.

It is well-known that there is a close correlation between the onset of diabetic retinopathy and loss of oxygen in the retina. See, for example, O. P. Van Bijsterveld (Editor), *Diabetic Retinopathy*, Martin Dunitz Ltd., London, (2000); N. D. Wangsa-Wirawan and R. A. Linsenmeier, "Retinal Oxygen: Fundamental and Clinical Aspects," *Arch. Opthalmol.* 121, 547-557 (2003); B. A. Berkowitz, R. A. Kowluru, R. N. Frank, T. S. Kern, T. C. Hohman, and M. Prakash. "Subnormal Retinal Oxygenation Response Precedes Diabetic-like Retinopathy," *Invest. Opthalmol. Vis. Sci.* 40, 2100-2105 (1999), and R. Roberts, W. Zhang, Y. Ito, and B. A. Berkowitz, "Spatial Pattern and Temporal Evolution of Retinal Oxygenation Response in Oxygen-Induced Retinopathy," *Invest. Opthalmol. Vis. Sci.* 44, 5315-5320 (2003).

Choroidal neovascularization has also been attributed to choroidal ischemias (Choroidal Neovascularization Correlated With Choroidal. Ischemia, Ann-Pascale Guagnini, MD; Bernadette Snyers, MD; Alexandra Kozyreff, MD; Laurent Levecq, MD; Patrick De Potter, MD, PhD *Arch Opthalmol.* (2006) 124:1063). Choroidal neovascularization can occur in the setting of age-related macular degeneration and is the leading cause of blindness in the age group of 65 years and older in the western countries.

Several patents disclose the use of compounds and pharmaceutical formulations for treating retinopathy or ocular ischemia. For example, U.S. Pat. No. 7,064,141 discloses a method for preventing, treating or inhibiting development of simple retinopathy and preproliferative retinopathy by use of a pharmaceutical composition having angiotensin II antagonistic activity. U.S. Pat. No. 6,943,145 discloses compounds and a method for the prevention and treatment of diabetic retinopathy. U.S. Pat. No. 6,916,824 discloses methods of treating cataracts and diabetic retinopathy with tricyclic pyrones. U.S. Pat. No. 6,156,785 discloses a method for increasing oxygen tension in the optic nerve and retina by administration of carbonic anhydrase inhibitors. U.S. Pat. No. 5,919,813 discloses the use of a protein tyrosine kinase pathway inhibitor in the treatment of diabetic retinopathy.

U.S. Pat. No. 7,074,307 discloses electrochemical sensors for the measurement of analytes in biological fluids. The patent discloses the production of oxygen by an electrode in order to allow the electrochemical sensor to function at sufficient oxygen levels independent of the oxygen concentrations in the surrounding environment.

U.S. Pat. No. 5,855,570 discloses an oxygen-producing bandage. The invention is a portable, self-contained device for the topical application of oxygen to promote the healing of skin wounds. The device includes a wound dressing that incorporates electrochemical, chemical, or thermal means for generating high purity oxygen. The device can regulate the supply of oxygen to an area above the wound at various concentrations, pressures and dosages. The device is driven by a built-in or accessory power source. Ambient air is brought into contact with a gas permeable cathode. Oxygen present in the air is reduced at the cathode to negative ions (i.e. peroxide, superoxide or hydroxyl ions) and/or their unprotonated and protonated neutral species. One or more of these species diffuse through an electrolyte and are then oxidized at a gas permeable anode to produce a high concentration of oxygen directly above the wound.

U.S. Pat. No. 4,795,423 discloses oxygenated perfluorinated perfusion of the ocular globe to treat ischemic retinopathy. The ocular globe is penetrated with two small cannulae and an inflow and outflow perfusion is established with an oxygenated perfluorochemical emulsion or other physiologically compatible oxygenated liquid at a rate and for a duration, sufficient to permit the natural healing process to occur.

However, there remains a need for precisely and controllably treating ischemic and pre-ischemic conditions in mammals. It would be particularly advantageous to treat such conditions without introducing chemicals into the biological tissue. There is a particular need for precisely and controllably treating ischemic and pre-ischemic conditions in such a manner in the eye, as commonly found in patients suffering from diabetic retinopathy.

SUMMARY OF THE INVENTION

These and other objectives, as will be apparent to those having ordinary skill in the art, have been achieved by providing a method and apparatus for the precise and controllable treatment of ischemic and pre-ischemic tissues.

The treatment involves supplying oxygen to ischemic or pre-ischemic body tissue by electrolysis of body fluid proximal to or within ischemic body tissue. When directed to ischemic tissue in the eyes, the treatment advantageously works in vitrectomized eyes as well as non-vitrectomized eyes. The method is based on selective and fractional electrolysis of the vitreous humor to produce oxygen, and optionally, active chlorine while simultaneously controlling pH.

The apparatus includes a tissue-implantable electrochemical system having an anode electrode in electrical contact with a first cathode electrode. The electrochemical system is designed to be implantable and operable in fluid-containing biological tissue and capable of the electrolytic production of oxygen from tissue fluid proximal to or within ischemic tissue when powered by a suitable power supply.

An object of the present invention is to treat an ischemic disease in a patient. Another object of the present invention is to delay or suppress the onset of diabetic retinopathy. This is accomplished by selective electrolysis of the vitreous humor and control of pH in both vitrectomized and non-vitrectomized eyes. The formation of free chlorine (i.e., chlorinous substances other than chloride) can either be allowed, or alternatively, controlled by being suppressed. The above strategy can be applied to appropriate organs and tissues to treat ischemic diseases in general.

For treating retinopathy (e.g., diabetic or other retinovascular diseases), vitreous humor can be selectively electrolyzed to produce predominantly molecular oxygen. In one embodiment, the formation of free chlorine is avoided. This can be accomplished by the selection of appropriate electrolytic mono- or multi-phase pulse patterns or taking advantage of the natural antioxidant properties of the vitreous humor. Aqueous humor is continuously produced and refreshed in the eye.

A second embodiment allows for the formation of free chlorine. Since the onset of retinopathy is believed to be a redox sensitive molecule such as cytochrome or hypoxia inducible factors, the presence of high potential free chlorine in the form of hypochlorite ions or hypochlorous acid can provide the signaling mechanism to avoid the onset of new and fragile vessel formation.

In accordance with one aspect of the present invention the foregoing and other objects are achieved by mono-, bi- or multi-phasic pulsed electrolysis of water to selectively produce oxygen and avoid the formation of free chlorine. Selective formation of oxygen can be achieved in multiple ways.

First, the electrical double layer which forms spontaneously at the surface of a metal electrode in sodium chloride solutions such as vitreous humor excludes chloride ions near the surface of the electrode. By judiciously injecting charge using the correct mono- or multi-pulsed time profiles, the water of the aqueous component of the vitreous humor can be selectively oxidized to molecular oxygen while simultaneously avoiding the oxidation of chloride ions to form free chlorine. The selected time profiles may be monophasic, biphasic or multiphasic.

Second, in the case of vitreous, even if low levels of free chlorine are formed, they will be converted to chloride because of the antioxidant properties of ascorbate, glucose and other reduced organic species that are naturally-occurring components of the vitreous.

Third, in one embodiment, free chlorine is electrolytically produced to maintain an oxidizing redox potential by the $ClO^-/Cl^-$ couple, which has a high oxidation potential, to provide the signaling mechanism to avoid the onset of new and fragile vessel formation.

Fourth, pH excursions that might be caused by electrolysis of a body fluid such as the vitreous humor can be corrected by use of a "pH clamp." In the absence of such a pH-controlling device, pH excursions can unfavorably alter the biochemistry of the vitreous humor. The pH clamp preferably uses three electrodes plus oxygen and/or pH sensors. In the case of the vitreous humor, two electrodes are preferably located in the vitreous while the third is preferably external to the ocular cavity (for example, implanted behind the ear of the patient). Information gathered by the sensors is used for selecting the operation of specific electrodes.

As described in further detail below, the operation of specific electrodes adjusts the pH and keeps the pH within a specified range. This approach advantageously prevents pH excursions beyond ranges that may have a detrimental effect on the normal biochemistry of body fluid, such as the vitreous humor.

The invention advantageously provides a treatment for ischemic and pre-ischemic tissues in mammals in a precise and controlled manner. In addition, the invention also achieves this without introducing chemicals into the biological tissue. The benefits of the invention are particularly advantageous for treatments of the eye since the eye is particularly sensitive to chemicals and invasive treatments.

BRIEF DESCRIPTION OF THE DRAWINGS

FIG. 7 presents data on the formation of oxygen and chlorine in phosphate buffered saline (PBS). The data are for 800 µA amplitude pulses with corresponding time durations presented on the abscissa. The time duration between pulses is 10 ms. Oxygen formation proceeds the formation of chlorine.

FIG. 8 contains data for the simultaneous formation of hydrogen and oxygen in PBS. The amplitude of the pulses was 800 µA and the duration of the pulses are presented on the abscissa. The time duration between pulses is 10 ms.

FIG. 12 shows results from a subgroup of rabbits which were treated with vitreous oxygenation after photothrombic vein occlusion.

FIG. 21 is a chart showing the correlation between steady state production of $O_2$ or $Cl_2$ under repetitive pulses at 100 Hz, 800 μA amplitude and pulse duration in phosphate buffered saline.

FIG. 22 is an illustration of the pH-control concept of the present invention.

DETAILED DESCRIPTION OF THE INVENTION

Figure 1:
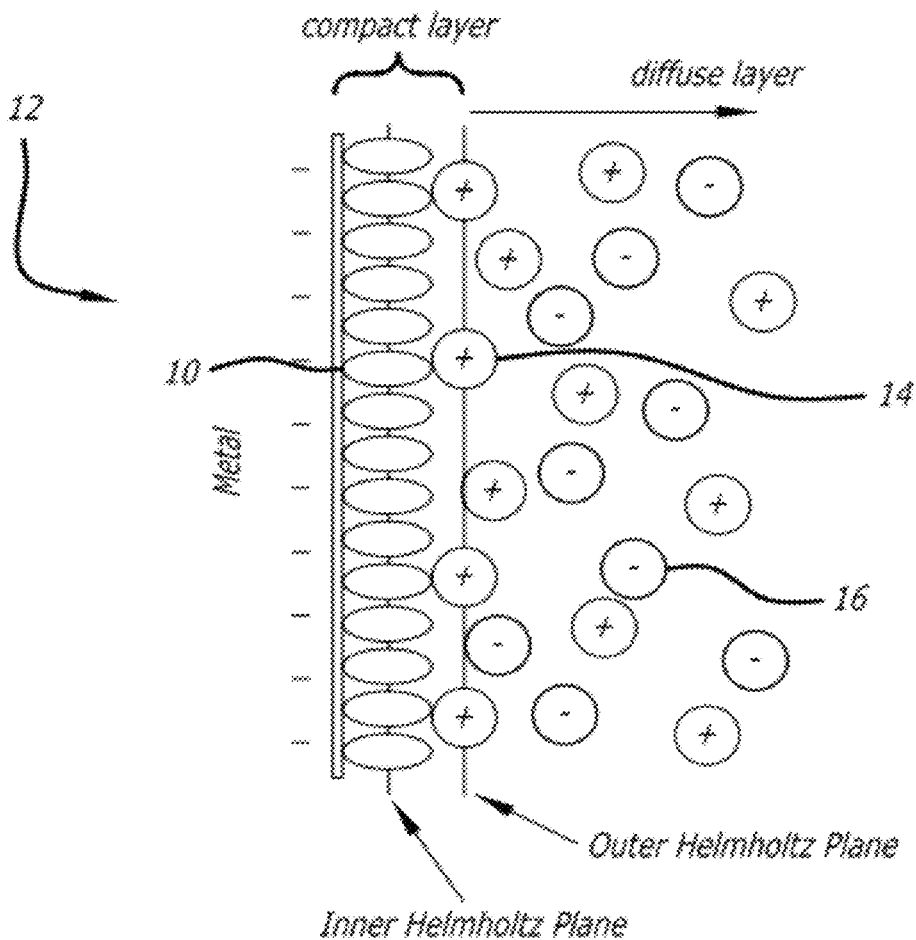
FIG. 1 is a schematic illustration of the structure of the electric double layer of a metal electrode dipping in an electrolyte solution such as sodium chloride, the primary electrolytic medium of vitreous humor. It is well known that the layer of water in immediate proximity to the metal electrode surface has a concentration of chloride ions lower than the bulk region (Butt et al., *Physics and Chemistry of Interfaces*, Wiley-VCH, 2003).

In one aspect, the invention is directed to a method for treating ischemic conditions or diseases in a mammal by treatment of the corresponding ischemic tissue. The ischemic tissue is any biological tissue suffering from lower than normal levels of oxygen, or any tissue considered predisposed or susceptible to lower levels of oxygen, i.e., pre-ischemic. The lower levels of oxygen are generally a result of a lower than required blood supply to specified body tissue. The mammal in need of treatment can be any mammal, most notably human.

Examples of ischemic tissues that can be treated include, but are not limited to, those associated with diabetic retinopathy in a patient's eye, retinopathy in a patient's eye caused by a retinovascular disease other than diabetes (e.g., vein and artery occlusions), retinopathy caused by choroidal ischemia (e.g., various forms of macular degeneration), ischemia in joint spaces (e.g., knee and shoulder), ischemia for cutaneous and subcutaneous spaces, ischemia in central and peripheral nervous systems (e.g., brain and spinal cord), ischemia of organs (e.g., heart, kidney, and organs of the gastrointestinal system), and ischemia on transplanted organs and tissue including stem cell transplants.

The method involves the electrolysis of body fluid in close or intimate contact with (i.e., proximal or within) ischemic tissue to increase the oxygen levels in the ischemic tissue. By "proximal" is meant an area of tissue containing biological fluid that is not necessarily within the ischemic tissue but maintains an intimate contact by exchange of biological fluid with the ischemic tissue undergoing treatment. Proximal tissue can also include tissue containing fluid that can act as a reservoir for higher oxygen concentrations where oxygen from the fluid can be diffused into the ischemic tissue. Some examples of fluid includes vitreous fluid, aqueous fluid, cerebrospinal fluid, or interstitial fluid such as lymphatics.

In a preferred embodiment, the electrolysis is conducted by implantation and electrical operation of an electrochemical system into the fluid of ischemic tissue. The implanted electrochemical system preferably includes an anode and a cathode (also referred to herein as a first anode or a first cathode).

The cathode operating in biological fluid will primarily reduce water to hydrogen according to the following half reaction:

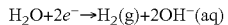
$$H_2O + 2e^- \rightarrow H_2(g) + 2OH^-(aq)$$

Superoxide anions and hydrogen peroxide can also form by cathodic reduction of dissolved oxygen. Though these species tend to be biologically toxic, the cellular enzymes superoxide dismutase and catalase are normally available for the efficient conversion of these species into non-toxic species.

The anode operating in biological fluid will oxidize water to oxygen according to the following half reaction:

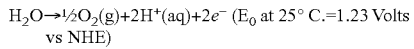
$$H_2O \rightarrow \tfrac{1}{2}O_2(g) + 2H^+(aq) + 2e^- \quad (E_0 \text{ at } 25^\circ C. = 1.23 \text{ Volts vs NHE})$$

Since biological fluid naturally contains chloride salts, the anode will additionally oxidize chloride ion to molecular chlorine according to the following half reaction:

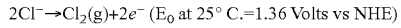
$$2Cl^- \rightarrow Cl_2(g) + 2e^- \quad (E_0 \text{ at } 25^\circ C. = 1.36 \text{ Volts vs NHE})$$

Although the chlorine half reaction has a higher standard potential than that of oxygen, it has a lower overpotential. Because of this, the chlorine oxidation reaction becomes significant during normal operation of the anode.

Molecular chlorine ($Cl_2$) produced at the anode immediately reacts with water to form various hydrolysis products of chlorine. The predominant hydrolysis products of chlorine include HOCl (hypochlorous acid) and its $ClO^-$ salts. In this application, chlorine and its hydrolysis products are also referred to as "chlorinous substances."

In one embodiment, production of chlorinous substances in biological fluid undergoing electrolysis is not controlled. This embodiment can be advantageous in certain situations where chlorinous substances are believed to have a beneficial effect. For example, as with oxygen, active chlorine can suppress or reverse the onset of diabetic retinopathy, other retinovascular diseases, and choroidal neovascularization. In addition, where chlorinous substances may not be advantageous, or perhaps even deleterious, these substances can, under certain circumstances, be rendered harmless by the natural antioxidant processes of the cell. As further discussed below, this is particularly true of the vitreous humor.

In another embodiment, the production of chlorinous substances in biological fluid undergoing electrolysis is controlled. This embodiment can be advantageous in certain situations where chlorinous substances are known or believed to be toxic, inflammatory, or deleterious in some other way. The production of chlorinous substances can be controlled by removal of chloride ion from the vicinity of the electrodes where electrolysis is being performed. The removal of chloride ion can be accomplished by any suitable method known in the art, including chemical or physical methods. Alternatively, the production of chlorinous substances can be controlled by converting produced chlorinous substances back to chloride or to other compounds that do not possess the same adverse effects. The conversion can be accomplished by any of the means known in the art, including chemical or physical methods.

In a preferred embodiment, the production of chlorinous substances is controlled by electrolytic means. By "controlled," is meant that the production of chlorinous substances is lessened by any amount, including to a point where chlorinous substances are considered not present or in trace amounts that are below the threshold of adverse effects. By one embodiment, the electrolytic means is a pulsed electrolytic technique capable of altering the location or concentration profile of chloride ions within an electrical double layer of the anodic electrode in such a manner that selective oxidation of water, and not chloride, is made possible. The pulsed electrolytic technique may be monophasic, biphasic, or multiphasic, and may include one, but more preferably, several successive pulses separated by a uniform, patterned, or variable time delay. Any suitable electrical (electrode) pulse generator can be used for generating the electrolytic pulses described herein.

A pulsed electrolytic technique as described above can accomplish such selective oxidation of water, by, for example, applying a succession of monophasic positive pulses having a duration shorter than the kinetic relaxation time constant for reestablishing the electrical double layer of the anode. In this manner, water is being selectively oxidized over chloride during the electrolytic pulse since chloride ion is not provided the necessary time to enter the microscopic layer of the electrical double layer containing only water. To lessen the oxidation of chloride, the pulse duration needs to be shorter than the relaxation time necessary for reestablishing the electrical double layer. The relaxation time varies according to electrode type, size, and chemical and physical conditions. Accordingly, a suitable pulse duration is very much dependent on the conditions encountered, and therefore, an appropriate pulse duration can vary substantially from one situation to another. For example, in one embodiment, a positive pulse is anywhere within a range having a minimum pulse time of about 50 microseconds (50 μs) and a maximum pulse of about 10 milliseconds (10 ms). More preferably, a positive pulse is within a range having a minimum pulse time of about 50 μs and a maximum pule time of about 500 μs. More preferably, the pulse duration can be in the range of about 100 to 200 μs.

The positive pulses are separated by a suitable time delay. The time delay is preferably long enough for the anode to reestablish the electrical double layer. For example, in one embodiment, the time delay is preferably within a range having a minimum of about 500 μs and a maximum of about 10 ms. In other embodiments, the time delay can be in the range of about 500 μs to 5 ms or 5 ms to 10 ms.

The water-chloride separation effect at the anode, as described above, can be accentuated by preceding (preconditioning) the positive pulse with a negative pulse of adequate duration. The negative pulse has the primary effect of repelling chloride ions further away from the electrode surface, thereby increasing the separation of water and chloride ion at the electrode surface. This method provides the beneficial effect of allowing for longer positive pulse durations prior to the onset of chlorinous compound formation. To be particularly effective for the foregoing purpose, the negative pulse has a duration preferably in the range of about 1 to 1000 μs. More preferably, the negative pulse is in the range of about 500 to 1000 μs. The time lapse between the negative pulse and the positive pulse is preferably in the range of about 1 to 1000 μs and more preferably about 500 to 1000 μs. The magnitude of the preconditioning voltage is preferably below the threshold for electrolysis.

In another embodiment, the production of chlorinous substances is controlled by applying a positive pulse for oxidation of water followed by a negative pulse of sufficient duration and voltage for reducing any remaining chlorinous substances to chloride ion salts. For example, hypochlorite ion is converted by the negative pulse to chloride ion according to the following half reaction:

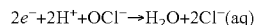

$$2e^- + 2H^+ + OCl^- \rightarrow H_2O + 2Cl^-(aq)$$

The water oxidation reaction at the anode and the water reduction reaction at the cathode in themselves combine without any change in pH. However, when water redox reactions are accompanied by formation of chlorine and its hydrolysis products, a drift toward lower pH occurs. Processes in the cell other than production of chlorinous substances can also cause a drift of the pH during electrolysis of biological fluid.

Figure 25:
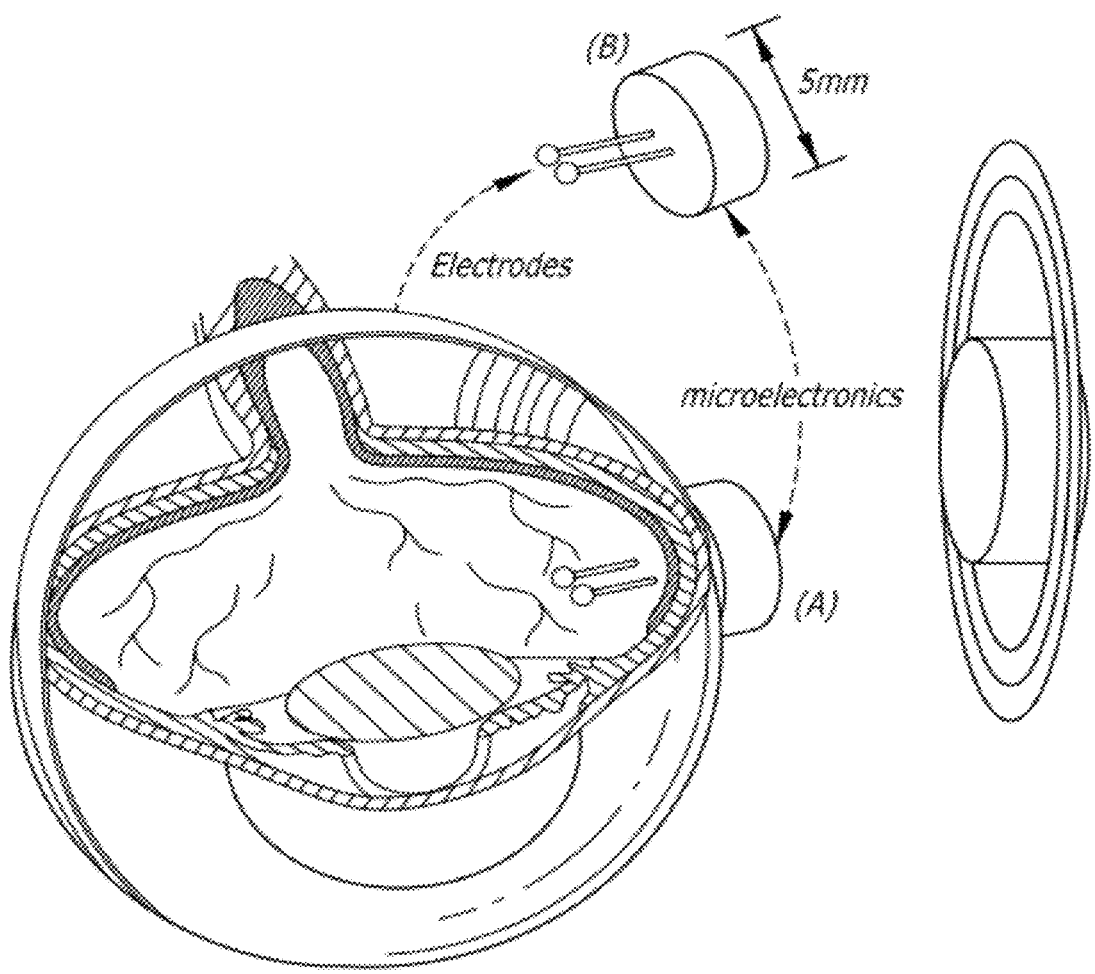
FIG. 25 illustrates an alternate view of the pH clamp as shown in FIG. 5. The second cathode is located outside the ocular cavity.

In order to prevent the pH from going beyond a range that may have a detrimental effect, the pH can be controlled by any suitable means known in the art. In a preferred embodiment, the pH is controlled by any suitable electrolytic means. Preferably, the electrolytic means involves implanting a second cathode in biological tissue or fluid that is proximal or adjacent to the region where the first anode and first cathode have been implanted, i.e., the "pH clamp" described earlier. The second cathode is preferably not in electrochemical contact (i.e., not in the same electrolyte compartment) with the first anode/cathode pair. For example, the second cathode is preferably external to the ocular cavity when the method is applied to ocular ischemic. See FIG. 25. Since the formation of oxygen in water lowers the pH, inclusion of a second operational cathode, which produces hydroxide ion, will have the effect of counterbalancing the lowered pH. The pH of the biological fluid undergoing electrolysis can be monitored by inclusion of a suitable pH sensor in the vicinity of where electrolysis is being conducted. Likewise, the oxygen level of the biological fluid undergoing electrolysis can be monitored by inclusion of a suitable oxygen sensor in the vicinity of where electrolysis is being conducted.

The second cathode can be operated within an electrochemical system not part of the first anode and cathode system (i.e., as part of a separate electrochemical compartment), or alternatively, electrically connected to the first anode and cathode which have been implanted in the biological fluid of ischemic tissue. Feedback information from the pH and/or oxygen sensors will cause either the first anode and first cathode, or the second cathode, or both, to operate at any given time in order to adjust the pH into a desired range.

The normal physiological range for biological tissue is in the range of about 6.5 to about 8.5. It is desirable in most cases to restrict the pH of biological tissues within this range. Depending on the application and the level of pH control required, the pH can be controlled in different ways, such as by controlling the production of chlorinous substances, or controlling the production of chlorinous substances in combination with use of a second cathode, or, by sole use of a second cathode. The pH can be controlled so as to remain within a range of about 6.5 to about 8.5, or more preferably about 6.5 to about 8.0, or even more preferably from about 6.5 to about 7.5.

In another aspect, the invention is directed to an apparatus for accomplishing the method described above. The apparatus includes the tissue-implantable electrochemical systems described above. The electrochemical system is capable of electrolytic production of oxygen from biological fluid proximal to ischemic tissue when the electrodes are implanted and made to operate by connection to a power supply source.

The connection to the power supply source need not be a physical (e.g., wired) connection. The connection may be, and in some instances may preferably be, in the form of a non-physical connection, such as a wireless electromagnetic transmission link between the electrochemical system and a wireless power supply source. In a wireless transmission device, the transmission of power is normally accomplished by interaction between adjacent mutually inductive devices such as coils that transfer energy by Faraday's Law of Electromagnetic Induction. The wireless power supply source needs to be capable of transmitting power via an electromagnetic frequency while the electrochemical system needs to be able to receive the electromagnetic transmission. The electromagnetic transmission can use any suitable electromagnetic frequency known in the art for transmitting power or information. The electromagnetic frequency used, can be, for example, based on an infrared, microwave, or a radiofrequency. More preferably, the transmission is based on a radiofrequency. The electrochemical system can be configured, if desired, to store the power transmitted for later use.

Examples of physically-connected power supplies that can be used to drive electrolysis in connection with the present invention include conventional batteries, fuel cells, biological fuel cells or bio-batteries or batteries powered by biomotion, and solar power devices.

The use of implanted electrodes for medical applications is well known (see e.g., J. Weiland, W. Liu and M. S. Humayun, "Retinal Prosthesis," *Ann. Rev. Biomed. Eng.* 7, 361-401 (2005)). Any of the electrodes known in the art that are suitable for implantation into biological tissue are considered suitable for the present invention. The electrodes can be of any suitable size, shape, and construction that permit them to be implanted and non-injurious to the subject under treatment. For example, in one embodiment, the electrodes are spherical in shape and constructed of platinum. The size of the electrodes is preferably within the range of about 0.1 to 10 mm, and more preferably, particularly for use in the eye, in the range of about 0.5 to 2 mm, and even more preferably about 1 mm. It is well known that the functional surface area of electrodes and catalysts can be made much larger than the apparent geometrical area. These techniques will be advantageously employed in this invention.

The distance between the first anode and cathode is preferably in a range of about 20 to 80 microns. More preferably, the distance between electrodes is about 30 to 70 microns, such as, for example, 50 microns.

Examples have been set forth below for the purpose of illustration and to describe the best mode of the invention at the present time. However, the scope of this invention is not to be in any way limited by the examples set forth herein.

EXAMPLE I

FIG. 1 is an illustration of the structure of the electric double layer at the metal electrolyte interface. The aqueous region 10 immediately surrounding electrode 12 has a lower chloride ion concentration than that of the bulk aqueous phase 16. The concentration of chloride ions increases with distance from the electrode surface until it reaches the bulk value. Chloride ion concentration at the outer Helmholtz plane 14 has an intermediate value.

Figure 2:
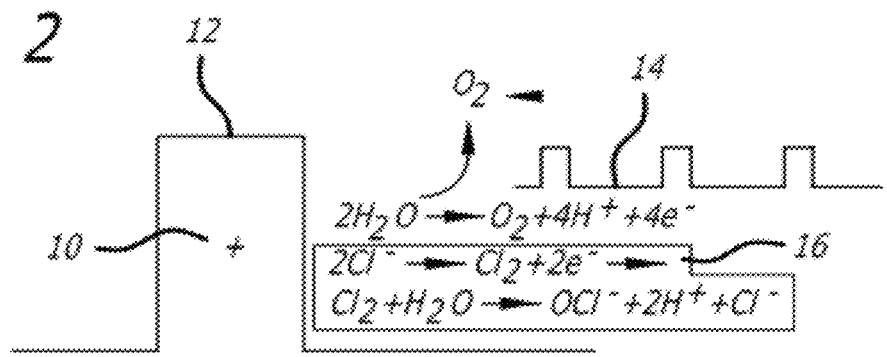
FIG. 2 is an illustration of the monophasic injection of a finite amount of positive charge into an electrode to oxidize the water that is in immediate proximity to the metal surface and depleted of chloride ions. To enhance the oxygen yield, the injection of positive charge can be preceded by a brief injection of negative charge to further expel chloride ions away from the electrode surface. This will enlarge the chloride-depleted region.

FIG. 2 illustrates the injection of positive charge 10 into the electrode. If the duration 12 of the pulse is less than the characteristic kinetic time constant for the movement of chloride ions to the surface of the electrode, water will be primarily oxidized to molecular oxygen at the anode while avoiding excessive formation of free chlorine. This is illustrated by the first equation 16 of FIG. 2, $2H_2O \rightarrow O_2+4H^++4e^-$. Chlorine gas, if formed, immediately reacts with water to form hypochlorite ions and hypochlorous acid. These equations, $2Cl^- \rightarrow Cl_2+2e^-$ and $Cl_2+H_2O \rightarrow OCl^-+2H^++Cl^-$ are shaded indicating that they do not occur because of the kinetic strategy that was used for oxidative charge injection. Following this injection, there is a natural kinetic relaxation time that is needed to reestablish the original structure of the electric double layer. This suggests a wait time 14 prior to injection of another positive charge.

Figure 9:
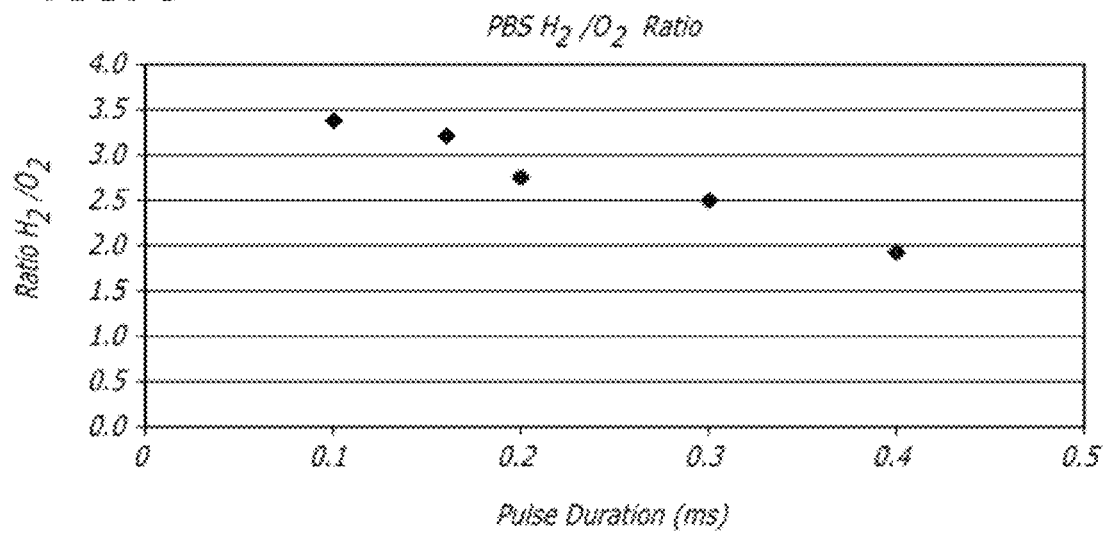
FIG. 9 presents a point-by-point calculation of the stoichiometric ratios of hydrogen to oxygen for the data points of FIG. 8.

As illustrated by the inset to FIG. 2, repetitive pulses can be used to preferentially produce oxygen instead of chlorine by waiting a period of time equal to or greater than the relaxation time required to reestablish the electric double layer structure. The data of FIG. 7 provides experimental proof of this aspect of the invention. Whereas oxygen is formed at pulse durations of 100 to 200 μs, no detectable chlorine is formed into this range of pulse durations. The onset of chlorine formation by the oxidation of chloride ions at the anode/electrolyte interface is kinetically slower than the onset of oxygen formation by the electrochemical oxidation of water. The data of FIG. 8 contains the simultaneous electrochemical formation of oxygen and hydrogen by the pulsed electrolysis of PBS. The oxygen data is the same as that presented in FIG. 7. FIG. 9 contains the corresponding stoichiometric ratios of hydrogen to oxygen in PBS. The ratio approaches two as the absolute amount of injected charge saturates the capacitance of the interfacial double layer.

EXAMPLE II

The preferential formation of oxygen over free chlorine can be enhanced by a preparatory injection of negative charge immediately followed by the injection of Faradaic positive charge for the production of oxygen. The formation of a higher absolute value of negative potential will contribute to the further depletion of chloride ions in the immediate proximity of the metal electrolyte interface. This will have the beneficial effect of lengthening the allowable pulse duration prior to the onset of free chlorine formation.

EXAMPLE III

Figure 3:
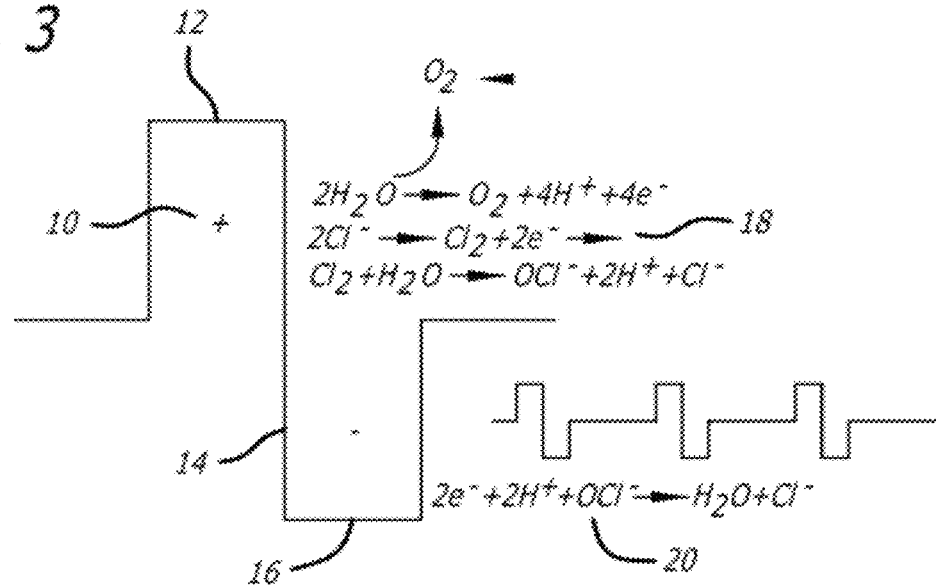
FIG. 3 illustrates a biphasic pulse that can be applied to reverse the formation of free chlorine. In this case the free chlorine that is formed during the anodic phase can be reduced to chloride during a cathodic phase that immediately follows the anodic phase.

Another method to reduce the formation of free chlorine is illustrated in FIG. 3. Following the formation of oxygen by positive charge injection 10 for duration 12, unwanted hypochlorite ions may form as illustrated by reactions 18. An immediate negative reversal pulse 14 for duration 16 will reduce the hypochlorite/hypochlorous acid back to chloride ions, illustrated by reaction 20, $2e^-+2H^++OCl^- \rightarrow H_2O+Cl^-$.

EXAMPLE IV

The variation of chloride ion concentration at the metal electrode-electrolyte interface follows a Boltzmann distribution, which is a continuous exponential dependence on distance. Therefore, some formation of free chlorine with increasing pulse duration is to be expected. The natural antioxidant properties of the vitreous humor can be used to further suppress the formation of free chlorine. Vitreous humor has the following composition: water, collagen fibrils, sugar, ascorbic acid, hyaluronic acid and inorganic salts, mostly sodium chloride. Sugar and ascorbic acid are good antioxidants in the context of reacting with free chlorine. Moreover, they are also good antioxidants for reacting with superoxide anions and hydrogen peroxide that may form at the cathode (in addition to the action of the superoxide dismutase and catalase, mentioned above).

Figure 4:
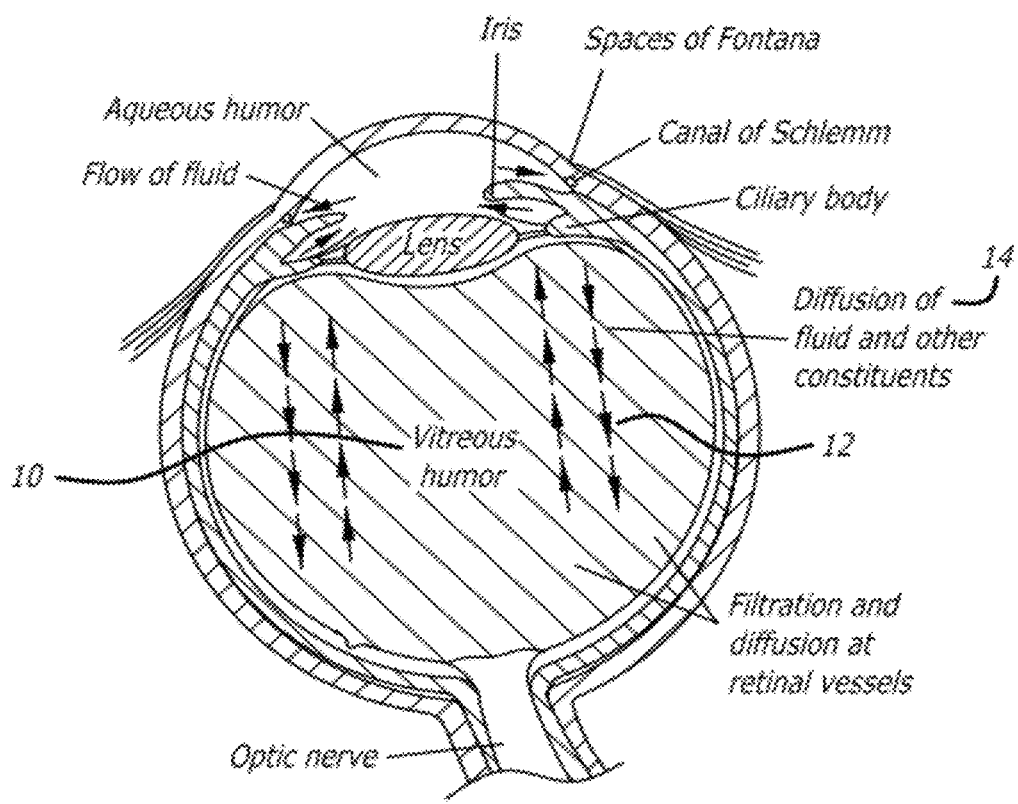
FIG. 4 illustrates a cross-section of a human eye with the natural flow of fluid and production of aqueous humor.
Figure 10:
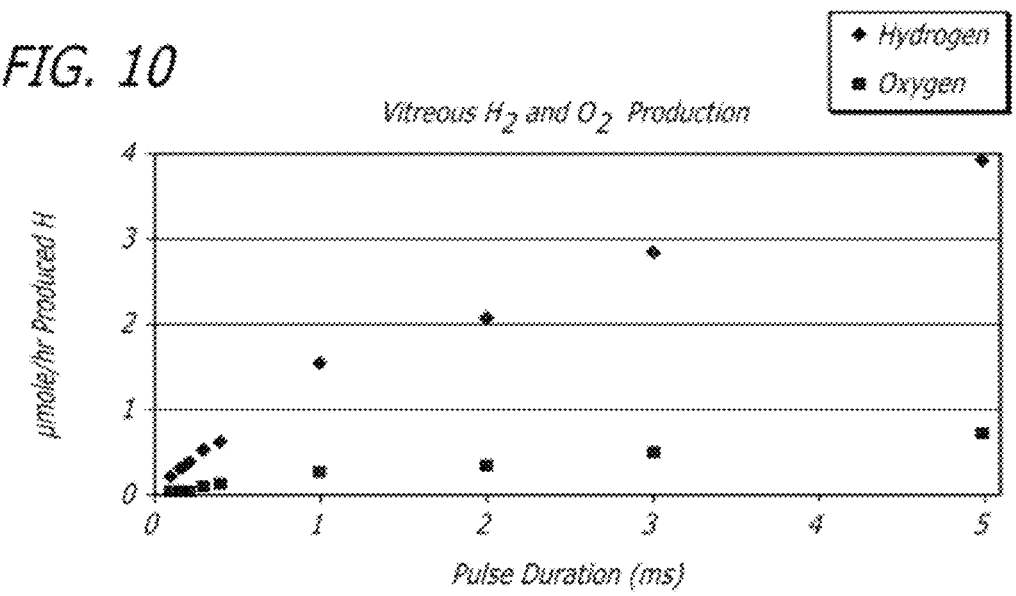
FIG. 10 contains data on the simultaneous electrochemical formation of hydrogen and oxygen in a medium containing a synthetic chemical formulation for vitreous humor. The amplitude of the pulses was 800 µA and the duration of the pulses are presented on the abscissa. The time duration between pulses is 10 ms.

Vitreous humor has a glucose concentration of 3.4 mM and an ascorbic acid concentration of 2.0 mM. Also, as illustrated in FIG. 4, aqueous humor 10 is naturally produced in the eye 12 at a rate of 2-3 μL per minute. Therefore, there is a steady-state supply 14 of both glucose and ascorbic acid. By setting an upper limit for the rate of free chlorine production and taking into account the natural antioxidant action of aqueous humor and its rate of production, one can set an upper limit for the rate of formation of free chlorine. FIG. 10 presents data on the simultaneous electrochemical formation of hydrogen and oxygen in a synthetic medium of vitreous humor. Under these conditions chlorine formation at the anode is quickly eliminated by its rapid reaction with ascorbate and its somewhat slower rate of reaction with glucose.

EXAMPLE V pH Clamp

Figure 5:
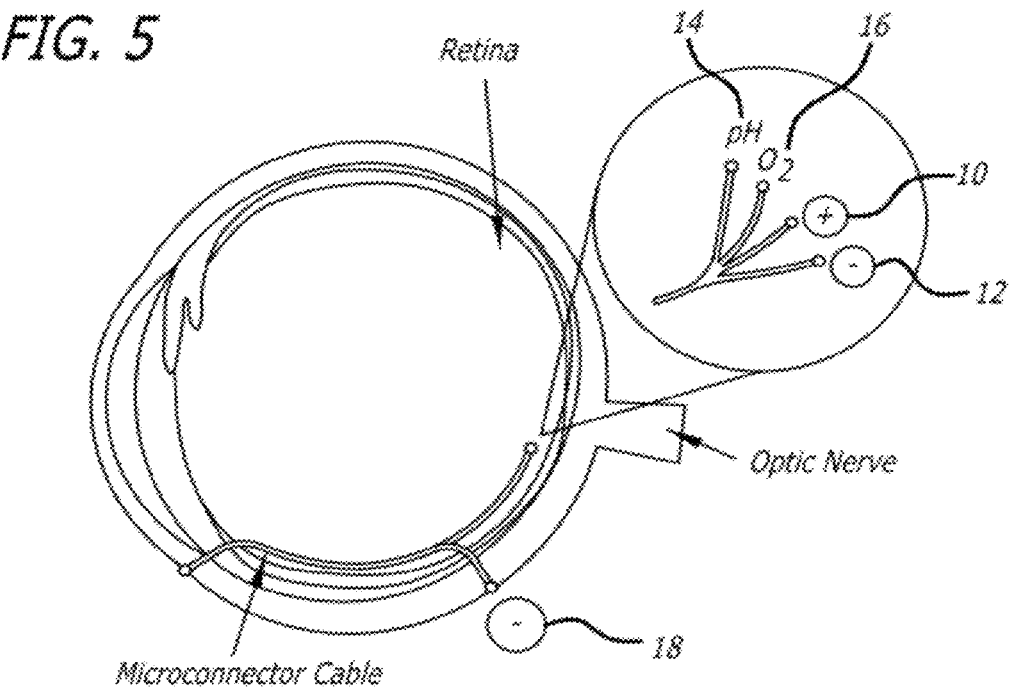
FIG. 5 illustrates one embodiment of the pH clamp. Cathode, anode, pH and oxygen sensors are located in close proximity to the region to be oxygenated. A second cathode is located outside the ocular cavity. As described below, the pH of the vitreous humor can be maintained within the desired range with this electrode configuration.

In performing the electrolysis of vitreous humor, at least three major electrochemical reactions occur. The two anodic reactions are $H_2O$ (liquid)→$½O_2$ (gas)+$2H^+$ (aq)+$2e^-$ and $2Cl^-$ (aq)→$Cl_2$ (gas)+$2e^-$. The major cathode reaction is $2H_2O$ (liquid)+$2e^-$→$H_2$ (gas)+$2OH^-$. The exclusive formation of hydrogen and oxygen produce compensating amounts of hydrogen ions and do not alter the pH. However, the oxidation of chloride ions to produce free chlorine does not involve hydrogen ion formation. Therefore, pH drift can occur. The solution to pH drift is to use the pH clamp illustrated in FIG. 5 (or as alternately shown in FIG. 25). The pH clamp is comprised of two intraocular electrodes 10 and 12 along with pH and $O_2$ sensors 14 and 16. When the oxygen sensor signals the onset of ischemia of retinal and choroidal tissue electrolytic production of oxygen/free chlorine (and hydrogen) may proceed. A third electrode 18 that is employed as an alternate cathode is also present.

Figure 6:
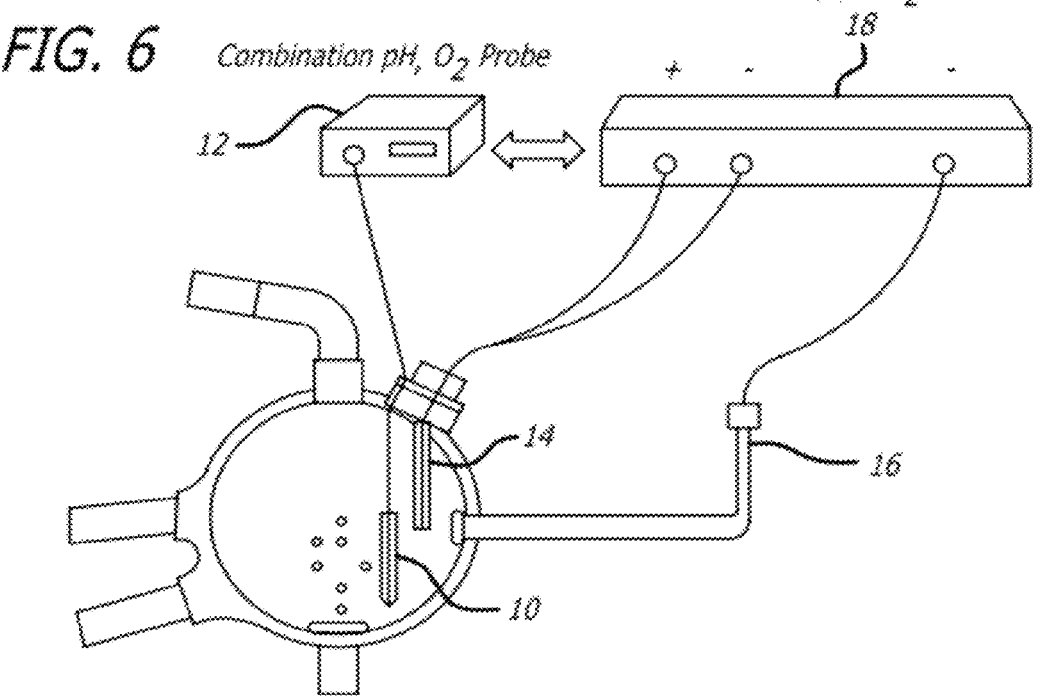
FIG. 6 is a model glass eye-chamber that replicates the physical chemistry of electrolysis in the eye and the three-electrode pH clamp. It was used to collect the data that demonstrate that the pH clamp works.

This second cathode is physically located outside the intraocular cavity, but is electrolytically connected to the vitreous humor by the conductive ionic pathways that exist in the natural fluids of the tissue. Depending on pH, an electronic switch can be used to connect the appropriate pair of electrodes that will maintain the pH within a specified range: FIG. 6 a model eye chamber that provides proof of principle for the pH clamp concept. FIG. 6 contains the chemical mixture that represents the vitreous humor. 10 is a pH probe. Two electrodes numbered 14 are in the "ocular cavity" whereas a third electrode (second cathode) 16 is located outside the cavity ("behind the ear") and separated by a fine frit in a tubular pathway that is filled with synthetic vitreous. The following tables contain experimental data for pH as a function of time for two electrode configurations:

TABLE 1

1 mA DC, Anode in the cell chamber and cathode in the side arm.

| Time (hr) | pH |
|---|---|
| 0 | 7.9 |
| 1 | 2.6 |
| 2 | 1.9 |
| 3 | 1.9 |

TABLE 2

1 mA DC, Cathode and anode in the cell chamber

| Time (hr) | pH |
|---|---|
| 0 | 7.7 |
| 1 | 8.1 |
| 2 | 9.1 |
| 3 | 9.3 |
| 4.75 | 9.4 |

These data demonstrate the strategy to clamp the pH to a predetermined level. If the cell cavity contains a single anode and the side arm contains a single cathode, the local pH of the cell cavity will become progressively more acidic because hydrogen ions are produced via water oxidation according to the reaction: $H_2O$→$½O_2$+$2H^+$+$2e^-$. The compensating hydrogen ion consuming reaction at the cathode is removed from the intraocular cavity and has negligible effect on alteration of local pH. However, if both electrodes are in the intraocular cavity, pH drifts in the opposite direction toward more basic values because of the difference in hydrogen ion production between water oxidation versus chloride ion oxidation. In the former, hydrogen ions are produced whereas in the latter they are not. The hydrogen-evolving cathode consumes hydrogen ions on a stoichiometric basis that exceeds the hydrogen ion production via the oxygen reaction by the equivalent amount of chloride ions that are oxidized.

EXAMPLE VI

Vitreous Oxygenation in Animals with Vein Occlusions

In a previous study, photothrombotic vein occlusions were successfully created in both rabbit and dog, and both were treated with intermittent vitreal oxygenation. The occlusions were confirmed with fluorescein angiography (FA) and retinal edema was analyzed with optical coherence tomography (OCT). Intraocular oxygen tension measurements were also performed using a fiberoptic fluorescence quenching system, as was an ELISA analysis of vitreous samples for VEGF. Due to the need for invasive techniques to directly measure retinal oxygen consumption, no firm value has been established for the rate of oxygen consumption of human retina. Multiple experimental techniques attempting to quantify oxygen consumption in holangiotic retina (Q $O_2$) have been performed with estimates ranging from 3.4 to 8.3 ml $O_2$/100 g/min in the light. Assuming a rate in the middle of this range of 5.0 ml $O_2$/100 g/min and a wet weight of canine/feline retina of 122 mg, the total oxygen consumption of the retina can be calculated as 6.1 μl $O_2$/min. Data from primate retina indicates a consumption rate of 0.5 μl $O_2$/min/cm$^2$ in the light, which using a retinal area of 11.89 cm$^2$ in humans, indicates an estimated oxygen consumption rate for the entire retina of roughly 5.94 μl $O_2$/min. These estimates of retinal oxygen consumption were used to guide further experimental oxygenation efforts.

Rabbits were initially used instead of dogs to establish the methodology to measure oxygen because of the lack of inner retinal blood flow and large pre-retinal oxygen tension gradients that exist over vascularized medullary wings and avascular retina. This allows for easy calibration of the oxygen probes. Moreover, vein occlusions lead to profound retinal ischemia making oxygen measurements easy. Briefly, pigmented rabbits underwent fluorescein angiograms (FA), color fundus photos, and optical coherence tomography (OCT), and vitreous samples for VEGF at baseline and then occlusions were created photothrombotically in the right eye. Following this, the animals were divided into three experimental groups; Control, Sham and Oxygenation. In the initial group, oxygen was delivered via direct administration into the vitreous and once an effect was established, electrolysis was used to generate the oxygen. In the initial group, control animals received no vitreous therapy, whereas Sham group animals had injections of room air (21% $O_2$) at a rate of 64 µL $O_2$/min for one hour at follow up day 3 and day 7, and Oxygenation group animals had 100% $O_2$ injected at 64 µL $O_2$/min for one hour also at day 3 and day 7 follow ups. At each follow up visit, all the animals had repeat color photos, FA, vitreous samples, oxygen recordings before and after vitreous injections and OCT imaging. At Day 14, the animals were sacrificed and the eyes harvested for histological analysis. Oxygen measurements were taken at multiple points (in the mid-vitreous as well as pre-retinal) at baseline and following occlusion using a fiberoptic oxygen sensitive probe (Oxford Optronix) This system based on fluorescence quenching has a range from 0 to 100 mmHg $O_2$ and has been used previously for intraocular oxygen recordings in human. Measurements were recorded in each position for a minimum of 30 seconds or until the reading stabilized.

In a (N=4) pilot series of rabbits, the following results have been found: 1) Vein occlusions were successfully created in all rabbits, and confirmed with FA; OCT confirmed the associated retinal edema; 2) Intraocular oxygen recordings were a) at baseline consistent with, published data from rabbit, and b) demonstrated marked decrease in post occlusion rabbits (see FIG. 11); 3) After oxygenation, pre-retinal and vitreous oxygen levels increased and vitreous levels of VEGF as measured by ELISA were much less elevated in animals receiving oxygenation (see FIG. 12). Note, that in this part of the study, the oxygen was applied intermittently for short periods and hence not likely to completely return VEGF levels to normal.

Figures 11, 12A, 12B:
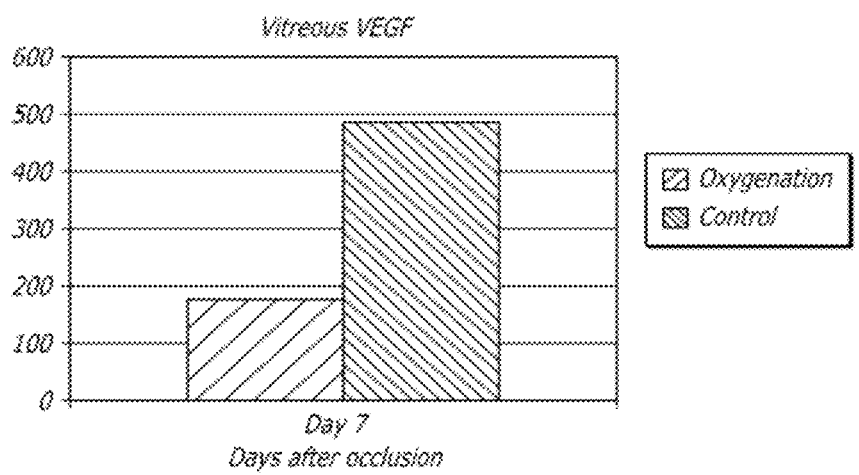
FIG. 11 shows data for photothrombic retinal vein occlusions in rabbits.

As shown in FIG. 11, retinal vein occlusions were performed in four rabbits. Data shown is from baseline (preocclusion), and three days after photothrombotic occlusion. Standard deviations are in parentheses. Intraocular oxygen recordings taken at different positions in the vitreous demonstrated marked reduction in oxygen levels after occlusion. OCT recordings demonstrated increased retinal thickness consistent with the edema seen on clinical exam. Vitreous samples analyzed for VEGF showed large increases in the VEGF levels in the post-occlusion state.

FIG. 12 shows results from a subgroup of rabbits which were treated with vitreous oxygenation after photothrombotic vein occlusion. 10A: Oxygen recordings taken 7 days following occlusion, before and immediately after one hour of oxygen delivery to the vitreous at the rate of 6 µL O2/min. Oxygen levels over the retina were considerably higher than the very low oxygen levels seen in animals with RVO before oxygenation (i.e., baseline recordings). P values are shown in parentheses. 10B: The percent increase in vitreous VEGF levels relative to pre-occlusion levels, at 7 days after occlusion. Treated animals were given one hour of oxygenation 3 days following occlusion. Oxygenated animals had a lesser degree of upregulation of VEGF within the vitreous. Note that because only one hour of oxygen was administered, VEGF levels were not expected to normalize.

Figure 13:
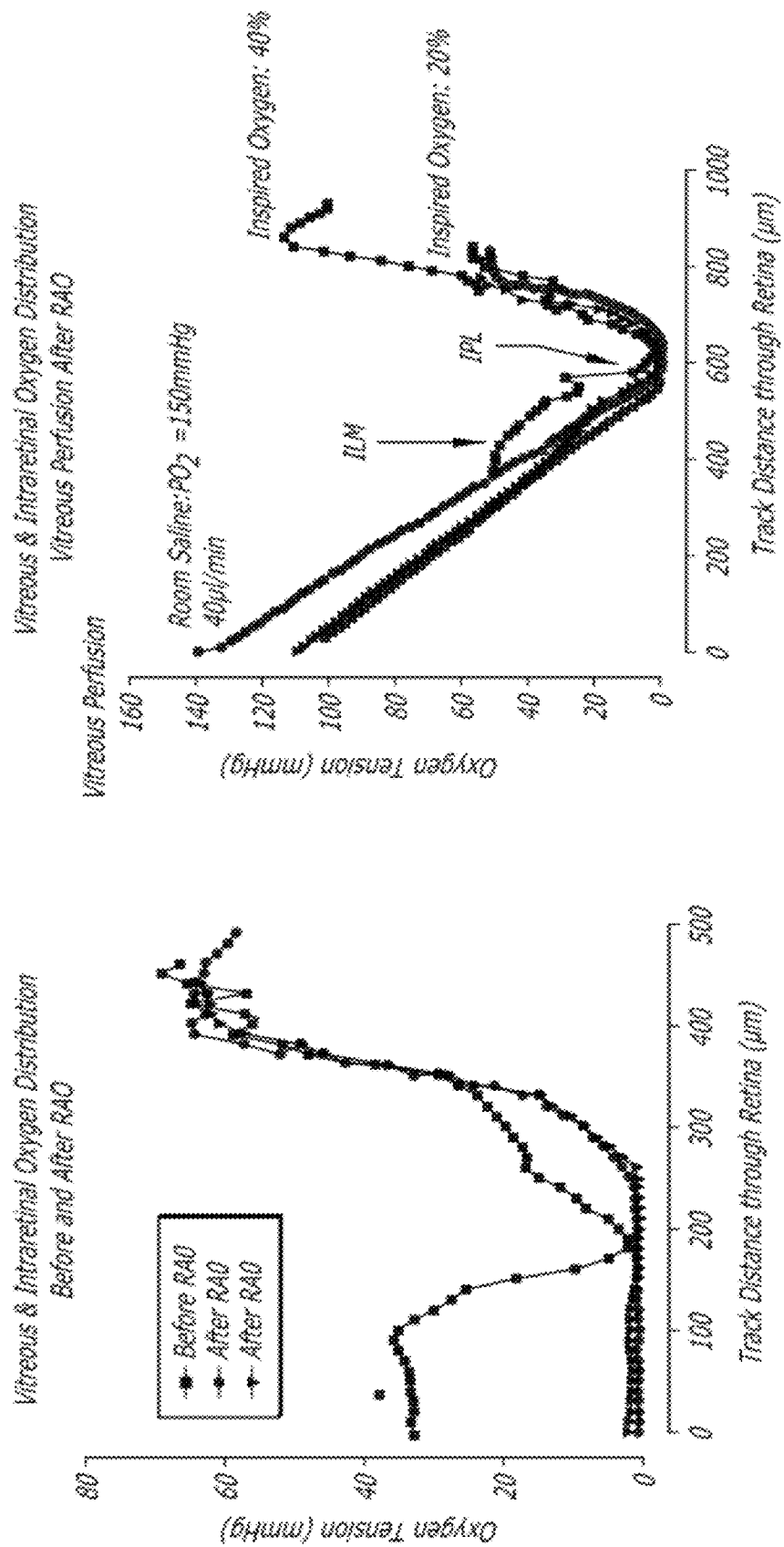
FIG. 13 shows intraretinal oxygen measurements before and after retinal artery occlusion.

In addition to vitreous and pre-retinal oxygen levels, it has been shown that intraretinal oxygen levels also increase in the animal model of RVO's (see FIG. 13). FIG. 13A shows markedly reduced levels of intraretinal oxygen after retinal artery occlusion. FIG. 13B shows increased pre-retinal oxygen levels as well as increased oxygenation in the retina especially to the inner retina after retinal artery occlusion and after increasing the oxygen in the vitreous.

Figure 14:
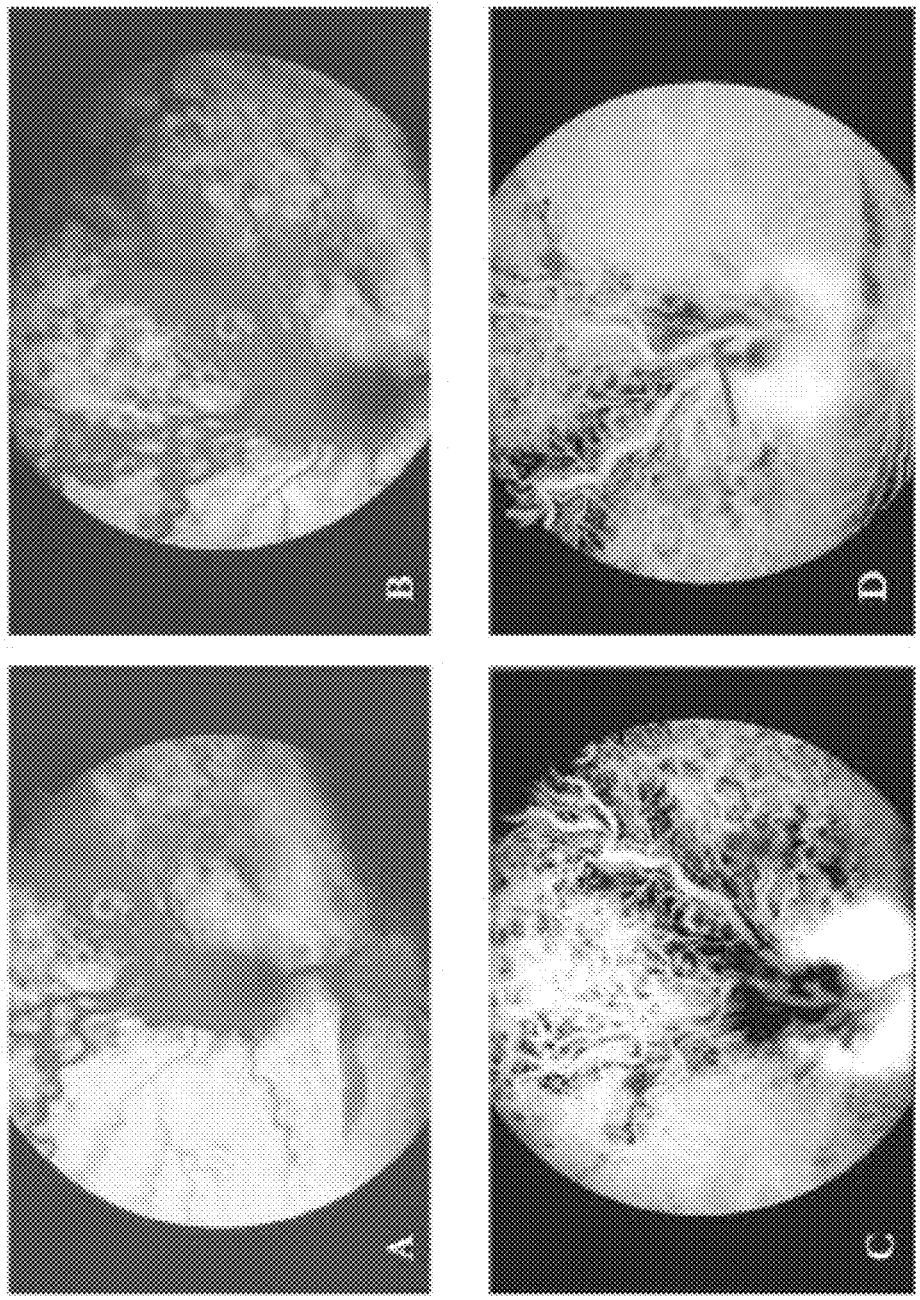
FIG. 14 shows fundus photos one week after photothrombosis in dog eyes.
Figure 15:
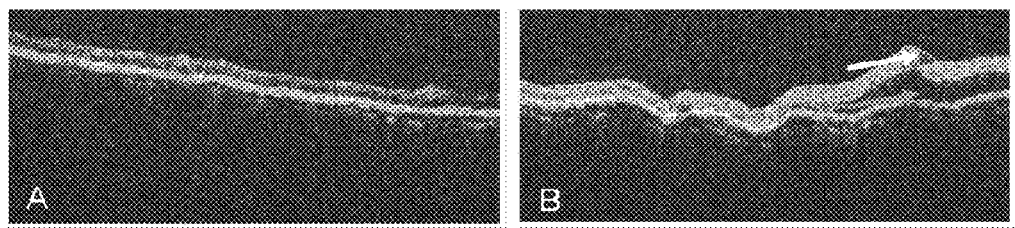
FIG. 15 shows OCT data from pre and post photothrombotic occlusion in dog retina.

In the second phase, electrolysis tests were advanced to dogs since positive results were already obtained with vitreal oxygenation in rabbits with RVO's. Dog eyes provide a holoangiotic retina, and the retinal blood vessels have autoregulation. They also are of a size closer to human and big enough for implanting the electrolysis electrodes. FIGS. 14 and 15 show the result of the procedure for inducing RVO's in dogs (see FIGS. 14, 15).

In FIG. 14, photos A and B show fundus photos one week after photothrombosis in dogs. The photos show dilated and tortuous retinal vessels, intraretinal hemorrhage and edma. Fluorescein angiography photos C and D show similar findings as well as the site of occlusion surrounded by leakage of dye (see arrow in D).

FIG. 15 shows OCT data from pre and post photothrombic occlusion in dog retina. Photo A shows an OCT image from an area of canine retina located inferiorly outside of the tapetum prior to occlusion. Photo B shows an OCT image from the same area of the retina four days following occlusion shows marked retinal edema, cystic changes within the retina (white arrow) as well as serous retinal detachment (red arrow). Images are each 2 mm×5 mm.

Figure 16:
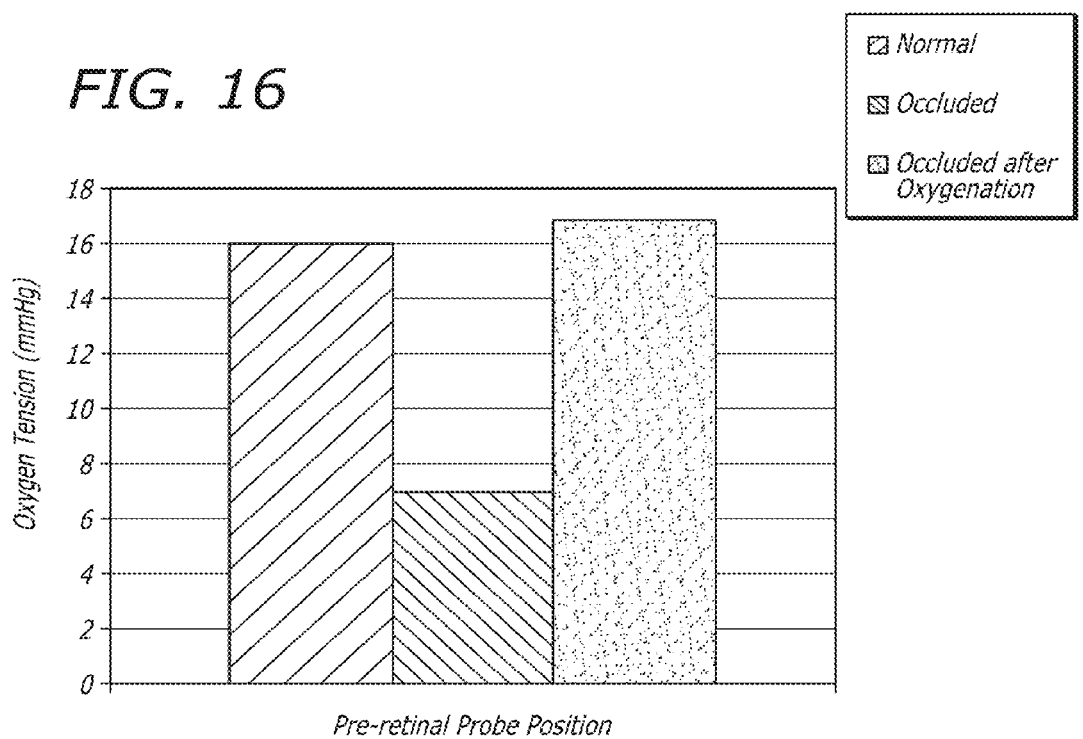
FIG. 16 shows results of short-term electrolytic oxygen production in a dog.

FIG. 16 shows the results of short-term electrolytic oxygen production in one dog. Oxygen recordings were taken in a preretinal location over normal retina and over retina that had undergone photothrombotic vein occlusion both before and after one hour of electrolytic oxygenation. A drop in pre-retinal oxygen levels with occlusion is demonstrated as well as the restoration of pre-retinal oxygen levels after one hour of electrolytic oxygen production. Bubble evolution was not visible and pH recordings always remained stable at 7.5.

After occlusion, intraocular oxygen recording were taken before and after one hour of electrolytic oxygen production within the vitreous. The electrolysis was carried out with two 1 mm sphere platinum electrodes surgically introduced via the pars plan and positioned in the anterior vitreous and stimulated with 800 µA monophasic pulses of 200 µs duration with a 1000 µs delay. A marked elevation of the oxygen gradients within the vitreous was observed (see FIG. 16). In order to extend the electrode metal half-life, biphasic pulses are also being studied.

Figure 17:
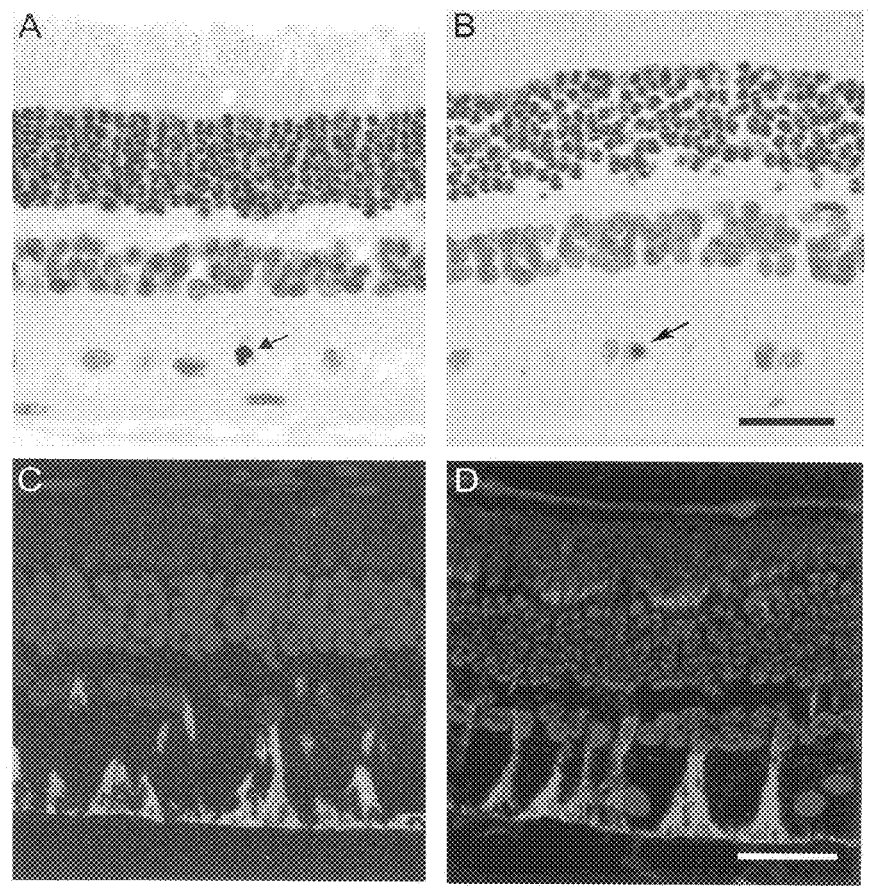
FIG. 17 shows the histology from control dog eyes which underwent occlusions and received no treatment and oxygenation in dog eyes which underwent occlusion followed by vitreal oxygenation at days 3 and 7.

As shown in FIG. 17, histological analysis (TUNEL and GFAP staining) revealed no difference between control dog eyes with RVO's and the intermittently oxygenation treated eyes. This can be considered an encouraging result as delivering oxygen through the vitreous did not result in increased toxicity to the retina. As for observing a protective effect, there was not expected to be a beneficial response because the oxygenation was intermittent and only delivered twice for one hour each time over the 14 day period after RVO.

FIG. 17 shows histology from control dog eyes which underwent occlusions and received no treatment (A, C) and oxygenation eyes which underwent occlusion followed by vitreal oxygenation at days 3 and 7 (B, D). The eyes were harvested post-occlusion day 14. Images A & B demonstrate TUNEL staining in control (A) and oxygenated eyes (B). TUNEL positive cells are indicated with black arrows and were equivalent in both groups. Images C/D demonstrate GFAP (green) and DAPI (blue) staining in control (C) and oxygenated eyes (D). There was no significant difference in the levels of both GFAP and DAPI staining. Bar=100 microns.

EXAMPLE VII

Surgical Implantation in Animals of Bioelectronics

Small subconjunctival, transscleral wires connecting the sclerally fixated bioelectronics with intraocular electrodes were implanted in animals. This approach places only the electrodes inside the eye while keeping the electronics outside. It is ideal because it minimizes the exposure of the retinal tissue to electrical, thermal and mechanical effects as well as makes it easier to surgically implant and explant. In one design, OXYGENERATOR electrodes that are foldable are used. These can be inserted through a 1 mm diameter incision whereas the remaining portion of the device is sutured extraocularly to the sclera under the conjunctiva.

Figure 18:
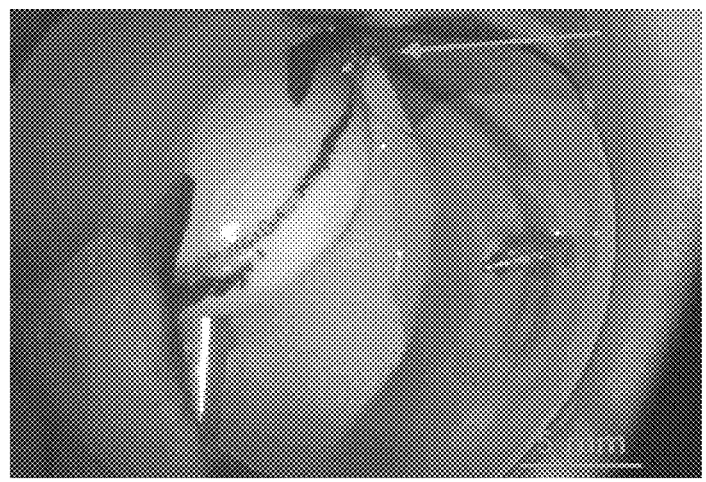
FIG. 18 is a photomicrograph showing a parylene electrode array in a dog eye after six months of implantation with very little gross inflammation and no signs of infection or retinal detachment.

FIG. 18 is a photomicrograph showing a parlyene electrode array in a dog eye after six months of implantation with very little gross inflammation and no signs of infection or retinal detachment. The arrow shows the site where the electrode array is transscleral. For the OXYGENERATOR electrode, the intraocular electrode array ends just inside the eye wall and not need to be tacked onto the retina as shown here.

EXAMPLE VIII

Science and Engineering of a Bioelectronic Oxygen Generator

Figure 19:
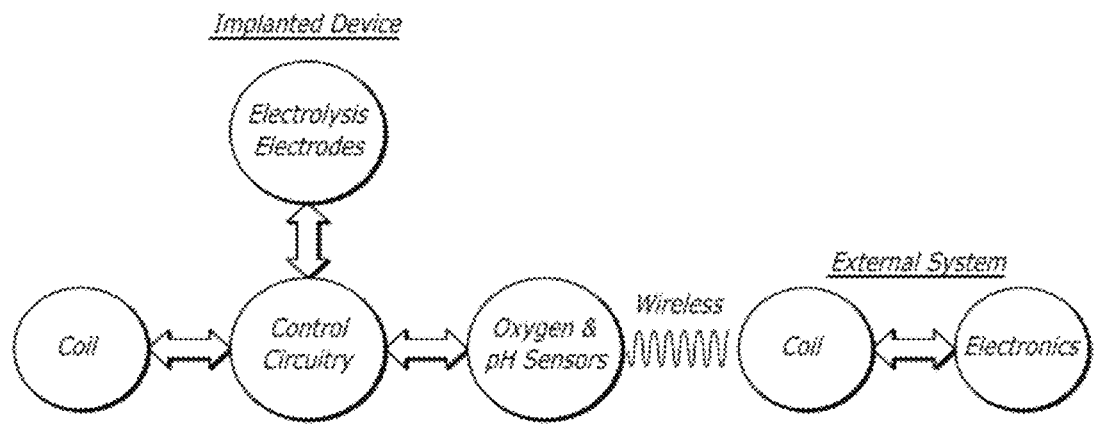
FIG. 19 is a generalized schematic of the system level design for the OXYGENERATOR electrochemical system.

An implantable device has been designed which raises dissolved O2 levels in the eye by select electrolysis of the intraocular fluid. Besides producing oxygen, sensors are used to monitor physiologically important parameters such as the dissolved oxygen levels and pH. The electrolysis circuit is under the feedback control of the sensors. RF coils are used to transfer power and data between the implanted device and external (wearable/portable) electronics. FIG. 19 shows a block diagram of the system.

The implanted part of the device not only has the telemetry receiving coil and the microelectronic circuitry to receive this radio frequency (RF) data and power link but also the ability to receive input from sensing electrodes and drive current through electrolysis electrodes. In FIG. 19, the second cathode electrode (third electrode) used for pH clamping is not shown. The external unit includes a transmitting coil, electronics, and battery. (not shown) that will activate the implanted unit. This wireless (e.g., radio frequency, RF) controller can be used during day or night. At night, it is possible for the transmitter coil to be in the pillow.

The main electrolysis components except the application specific integrated chipset (ASIC) have been prototyped with microelectromechanical systems (MEMS) engineering using parylene, a biomaterial with the highest possible FDA biocompatibility rating i.e, class VI FDA biomaterial. Using advanced electroplated platinum techniques, an effective surface area can be obtained that exceeds the actual electrode area by 50×. This increases the efficiency of electrolysis hence requiring less power to produce more $O_2$ per apparent geometric area. Similarly, by controlling the distance between the anode and cathode to 50 microns, pH fluctuations can be prevented.

Figure 20:
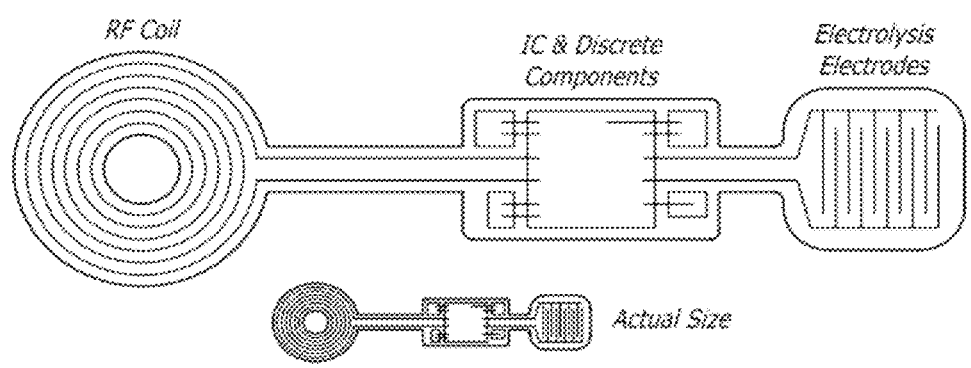
FIG. 20 is a schematic showing the approximate size of the proposed implant.

Specifically, given the efficiency of the electrolysis electrode design, the required 6 µL/min rate of oxygen production at T=37° C. and P=15 mm Hg can be attained while consuming only 9 mL/min of intraocular fluid (less than 1% of what is produced per minute by the eye normally) using a very nominal 3 mW of power. In fact, the total power consumption for the entire device including the discrete components for the inductive (RF) link, as well as ASIC and the cantilever sensors is less than 10 mW, which will result in no observable temperature increase in the tissue. Moreover, a flexible 5-layer implantable coil has been built. This implanted receiver coil with an outer diameter of 10 mm and an inner diameter of 3 mm operating at a frequency of 2 MHz is capable of wirelessly transmitting the needed power levels. The ASIC design also uses standard CMOS process that makes it easy to fabricate. The coil combined with the ASIC, limited number of discrete electronic components, and electrolysis electrodes creates a compact and flexible package suitable for long-term implantation. The incision in the eye wall to introduce the foldable electrodes would be less than 1 mm in diameter and the rest of the device on a flexible substrate with a soft polymer consistency can be easily sutured to the eye wall under the conjunctiva limiting the risk of exposure. A diagram showing the approximate size of the implant is shown in FIG. 20.

EXAMPLE IX

Selective Electrolysis of Saline Solution

Although state-of-the-art sensors and shutdown features capable of sensing and reacting to a significant pH change or presence of toxic byproducts can be included, even such a protectively-equipped process is not foolproof against such possibly adverse situations. Therefore, additional protective features can be included, such as pulsed eletrolysis methods for the selective production of oxygen over chlorinous byproducts. Moreover, $O_2$ and $H_2$ will not back react on the platinum electrodes because of the geometric design and low temperature (37° C.).

FIG. 21 contains kinetic data for 0.85 mm platinum diameter electrodes with PBS and demonstrates the kinetic time course for the onset of oxygen and chlorine evolution. PBS, a buffered 0.15 M NaCl solution, contains approximately the same concentration of NaCl as human vitreous humor. As mentioned above, except for a low level of specific chemisorption, chloride anions are largely excluded from the inner and outer Helmholtz planes, the regions of the electrolyte that are immediately adjacent to the electrode. The extent of exclusion can be estimated from the Debye length ($\lambda_D$) which, for the case of physiological temperature and saline (37° C. and 0.15 M NaCl), is $\lambda_D$=0.78 nm. Each data point represents the steady-state production of oxygen or chlorine for 100 Hz repetitive anodic pulses of 800 µA and 0-400 µs pulse duration. The onset of chlorine production occurs at a 200 µs pulse width. That is to say, sufficiently rapid injection of positive charge into the anode can complete the oxidation of water to molecular oxygen prior to the movement of bulk chloride ions to the electrode surface where the Cl⁻ is oxidized to chlorine. Oxygen and the coevolved hydrogen were detected in the gas phase using flow comprised of an electrogalvanic cell for the oxygen sensor and a tin oxide semiconductor for the hydrogen sensor. The production of free chlorine was detected in a standard spectrophotometric assay based on the rapid and quantitative oxidation of ascorbic acid. The time between pulses was 10 ms, a value much longer than the relaxation time of the electric double layer which is in the nanosecond range. It is also longer than the RC time constant discharge of the double layer capacitance. FIG. 21 is an original discovery associated with this proposal which shows that the structure of the electric double layer can be used to selectively oxygenate tissue in chloride ion containing fluids without the corresponding electrolytic formation of free chlorine. Interestingly, this is the inverse goal of the chlor-alkali process, one of the oldest industrial processes, in which the aim is to maximize the production of chlorine by the electrolysis of brine. It may also be possible to extend the half-life of the platinum electrodes by use of charge-balanced symmetric and asymmetric biphasic current pulses.

Figure 23:
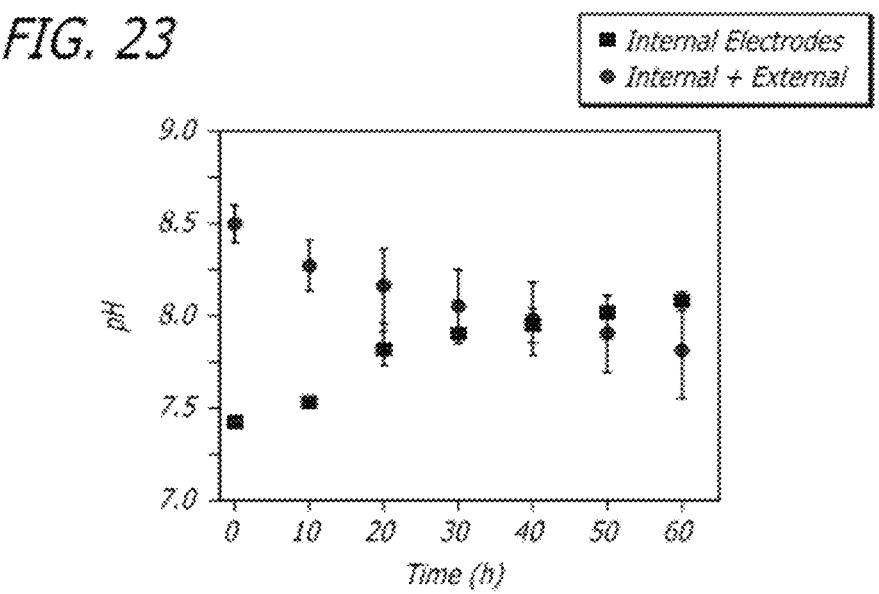
FIG. 23 is a chart showing pH shift during electrolysis of Ames medium plus 200 μg per ml of hyaluronic acid.
Figure 24A:
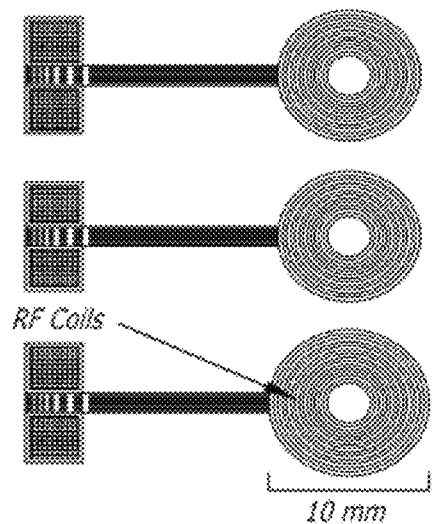
FIG. 24 shows photos of parylene-encapsulated electrodes and coils.
Figure 24B:
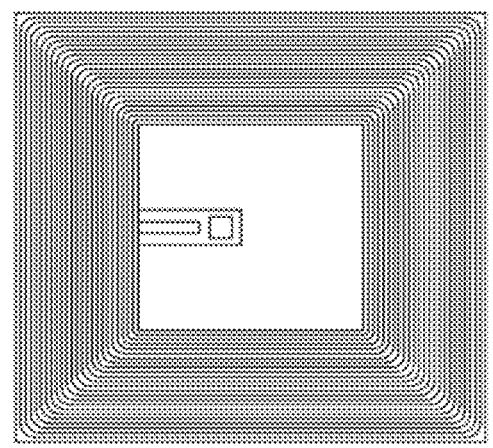

The pH Clamp Although vitreous humor is primarily physiological saline, it contains other components such as hyaluronic acid, glucose, ascorbate, collagen fibrils, etc. Even if chlorine formation was completely suppressed, the pH may still drift. Accordingly, a pH clamp, as specially designed for the present invention, can be used. The pH clamp uses a three electrode configuration to maintain constant pH under all conditions of oxygenation of the vitreous. FIGS. 22 and 23 illustrate the idea. The anode is the source of oxygen. The cathode is the source of hydrogen. Two cathodes are illustrated. One cathode is in the intraocular cavity, adjacent to the anode. The other cathode is located outside the ocular cavity, but is electrically connected to it via the ionic conductivity of the tissue. Which pair of electrodes is used for the electrolysis is determined by the pH sensor and the electronic feedback switching circuit that selects the electrodes. A photograph of the experimental chamber is presented in the inset in FIG. 22. The data of FIG. 23 represent electrolysis of 800 µA for one hour of Ames medium+200 µg per ml hyaluronic acid. Note that the starting pH of this solution was 7.4 and that, while using the internal electrodes, there is a slight increase in the pH which in the eye should be buffered by the vitreous. But should the electrolysis begin to show such a pH drift while in the eye (i.e., the pH would increase becoming more basic because of the chlor-alkali process), the cantilevered pH sensors would detect this and switch the device into a mode of using the extraocular electrode. With the cathode external to the vitreous cavity, the pH becomes acidic. This is because the oxidation of water generates four moles of protons per mole of oxygen, $2H_2O \rightarrow O_2+4H^++4e^-$. By selecting the external electrode, the pH can be reduced, thereby restoring the pH to its original value. It is this ability to alternately select the appropriate pair of electrodes that provides constant pH control inside the eye. Although this strategy is a technical fix to the problem of oxygenating the vitreous under pH neutral conditions, it does not, of course, change the overall chemistry of electrolysis. It "exports" the pH problem outside the eye to the area of the extraocular cathode in the subconjunctival space where pH change can be treated easily as the volume of subconjunctival fluid is $10^6 \times$(million times) greater and acts as a buffer. These data demonstrate the feasibility of the approach.

Oxygen and hydrogen evolution are by far the major electrolytic reactions at the anode and cathode. The objective of the repetitive pulsing strategy is to suppress formation of free chlorine, $Cl_2$. However, should it form, it quickly reacts with water to form hypochlorite ions, $OCl^-$, and hypochlorous acid, $HOCl$ which has a pKa of 7.53. Electrolytic formation of molecular hydrogen, $H_2$, can be ignored. It is unreactive under experimental conditions in the eye. The inset in FIG. 22 illustrates minor pathways that can potentially form superoxide anions, $O_2^-$, and hydrogen peroxide, $H_2O_2$. However, these species are normally efficiently eliminated by the natural superoxide dismutase and catalase activity in the vitreous. Moreover, ascorbate and glucose, which have antioxidant activity, are present at millimolar concentrations in the vitreous.

While there has been shown and described what are at present considered the preferred embodiments of the invention, it will be obvious to those skilled in the art that various changes and modifications can be prepared therein without departing from the scope of the inventions defined by the appended claims.

What is claimed is:

1. A method of treating ischemic tissue in a mammal that contains or is proximal to biological fluid and that is proximal to other tissue, the method comprising:
    implanting an anode and a first cathode into the biological fluid, wherein a path is created between the anode and the first cathode for current to flow;
    implanting a second cathode in the other tissue and not within the biological fluid, wherein a second path is created between the anode and the second cathode which is through the biological fluid and through the other tissue between the anode and the second cathode;
    implanting a pH and/or oxygen sensor within the biological fluid configured to detect the level of pH and/or oxygen within the biological fluid; and
    applying a voltage potential between the anode and tie first cathode and also between the anode and the second cathode which is configured to supply the ischemic body tissue with oxygen due to electrolysis of the biological fluid; while at the same time maintaining the pH level within the biological fluid within a pre-determined range as detected by the pH and/or oxygen sensor.

2. The method of claim 1, wherein formation of chlorinous substances in biological fluid undergoing electrolysis is controlled.

3. The method of claim 2, wherein formation of chlorinous substances is controlled by a pulsed electrolytic technique capable of altering the location or concentration profile of chloride ions within an electrical double layer of the anode electrode so as to permit selective oxidation of water in body tissue to oxygen.

4. The method of claim 3, wherein a positive pulse having a duration shorter than the kinetic relaxation time constant for reestablishing the electrical double layer at the anode is preceded by a negative pulse to heighten chloride depletion from water at the electrode surface.

5. The method of claim 3, wherein the technique comprises a positive pulse for oxidation of water followed by a negative pulse of sufficient duration and voltage for reducing any remaining chlorinous substances to chloride ion salts.

6. The method of claim 1, wherein the ischemic tissue is located in an eye and the biological fluid is vitreous humor.

7. The method of claim 3, wherein the pulsed electrolytic technique uses a monophasic, biphasic, or multiphasic electrical pulse technique.

8. The method of claim 7, wherein the technique comprises a monophasic positive pulse having a duration shorter than the kinetic relaxation time constant for reestablishing the electrical double layer.

9. An apparatus for delivering oxygen to ischemic tissue in a mammal that contains or is proximal to biological fluid and that is proximal to other tissue, the apparatus comprising:
    an anode and a first cathode configured to be implanted into the biological fluid, wherein a path is created between the anode and the first cathode for current to flow;
    a second cathode configured to be implanted into the other tissue and not within the biological fluid, wherein a second path is created between the anode and the second cathode which is through the biological fluid and through the other tissue between the anode and the second cathode;

a pH and/or oxygen sensor configured to be implanted within the biological fluid and configured to detect the level of pH and/or oxygen within the biological fluid; and a power supply source configured to apply a voltage potential between the anode and tie first cathode and also between the anode and the second cathode which is configured to supply the ischemic body tissue with oxygen due to electrolysis of the biological fluid; while at the same time maintaining the pH level within the biological fluid within a pre-determined range as detected by the pH and/or oxygen sensor.

10. The apparatus of claim 9, wherein the apparatus further comprises means for controlling the formation of chlorinous substances in the biological fluid while it is undergoing electrolysis.

11. The apparatus of claim 10, wherein the means for controlling the formation of chlorinous substances is an electrode pulse generator in contact with the anode.

* * * * *

UNITED STATES PATENT AND TRADEMARK OFFICE
CERTIFICATE OF CORRECTION

| | | |
|---|---|---|
| PATENT NO. | : 8,209,024 B2 | |
| APPLICATION NO. | : 12/523990 | |
| DATED | : June 26, 2012 | |
| INVENTOR(S) | : Elias Greenbaum and Mark S. Humayun | |

It is certified that error appears in the above-identified patent and that said Letters Patent is hereby corrected as shown below:

At col. 14, line 36, "recording" should read --recordings--.

At col. 14, line 40, "pars plan" should read --pars plana--.

Signed and Sealed this
Twenty-third Day of October, 2012

David J. Kappos
*Director of the United States Patent and Trademark Office*